US005750653A

United States Patent [19]
Chu et al.

[11] Patent Number: 5,750,653
[45] Date of Patent: May 12, 1998

[54] PROTEIN, FAF1, WHICH POTENTIATES FAS-MEDIATED APOPTOSIS AND USES THEREOF

[75] Inventors: Keting Chu, Burlingame; Lewis T. Williams, Tiburon, both of Calif.

[73] Assignee: The Regents of the University of California, Oakland, Calif.

[21] Appl. No.: 477,476

[22] Filed: Jun. 7, 1995

[51] Int. Cl.$^6$ .................. C07K 14/705; G01N 33/53; A61K 38/17

[52] U.S. Cl. .................. 530/350; 435/7.1; 435/69.7; 514/2

[58] Field of Search .................. 530/350; 435/7.2, 435/69.7; 514/2

[56] References Cited

U.S. PATENT DOCUMENTS

| | | | |
|---|---|---|---|
| 5,106,762 | 4/1992 | Bredehorst et al. | 435/546 |
| 5,338,678 | 8/1994 | Senter et al. | 435/227 |
| 5,503,977 | 4/1996 | Johnsson et al. | 435/6 |
| 5,563,039 | 10/1996 | Goeddel et al. | 435/7.1 |

OTHER PUBLICATIONS

Suda et al J. Exp. Med (1994) vol. 179: pp. 873–879.
Remington's Pharmaceutical Sciences (1990) 18th ed pp. 276–268, 821–822 (Gennard et al eds) Philadelphia Coll. of Pharmacy & Science, Phila., PA.
1994 SIGMA Biochemicals and Organic Compounds pp. 751 & 1021 Catalogue, SIGMA Chemical Co, St. Louis MO.
Amaya et al., "FGF signalling in the early specification of mesoderm in Xenopus," *Development* 118:477–487 (1993).
Brodsky et al., "Analysis of the site in CD4 that binds to the HIV envelope glycoprotein," *Journal of Immunology* 144(8):3078–3086 (1990).
Durfee et al., "The retinoblastoma protein associates with the protein phosphatase type 1 catalytic subunit," *Genes & Development*, 7:555–569 (1993).
Itoh et al., "The polypeptide encoded by the cDNA for human cell surface antigen Fas can mediate apoptosis," *Cell*, 66:233–243 (1991).
Klippel et al., "A region of the 85–kilodalton (kDa) subunit of phosphati–dylinositol 3–kinase binds the 110–kDa catalytic subunit in vivo," *Mol. Cell. Biol.*, 13(9):5560–5566 (1993).

Nagata, "Mutations in the Fas antigen gene in lpr mice," *Immunol.*, 6:3–8 (1994).
Sato et al., "FAP–1: a protein tyrosine phosphates the associates with Fas," *Science*, 268:411–415 (1995).
Watanabe–Fukunaga et al., "The cDNA structure expression, and chromosomal assignment of the mouse Fas antigen," *J. Immunol.*, 148(4):1274–1279 (1992).
Watanabe–Fukunaga et al., "Lymphoproliferation disorder in mice explained by defects in Fas antigen that mediates apoptosis," *Nature*, 356:314–317 (1992).
Boldin, et al., "A Novel Protein that Interacts with the Death Domain of Fas/APO1 Contains a Sequence Motif Related to the Death Domain", *J. Biol. Chem.* 270(14):7795–7798 (1995).
Chinnaiyan, et al., "FADD, a Novel Death Domain–Containing Protein, Interacts with the Death Domain of Fas and Initiates Apoptosis", *Cell*, 81:505–512 (1995).
Chu, et al., "A Novel Protein, FAP, Potentiates Fas–mediated Apoptosis", *Journal of Investigative Medicine*, 43(suppl. 2):289A (1995).
Cleveland, et al., "Contenders in FasL/TNF Death Signaling", *Cell*, 81:479–482 (1995).
Hsu, et al., "TNF–Dependent Recruitment of the Protein Kinase RIP to the TNF Receptor–1 Signaling Complex", *Immunity*, 4:387–396 (1996).
Johnson, "The Arabidopsis thaliana myo–Inositol 1–Phosphate Synthase (EC 5.5.1.4)", *Plant Physiol.*, 105:1023–1024 (1994).
Stanger, et al., "RIP: A Novel Protein Containing a Death Domain That Interacts with Fas/APO–1 (CD95) in Yeast and Causes Cell Death", *Cell*, 81:513–523 (1995).

*Primary Examiner*—Stephen Walsh
*Assistant Examiner*—Daryl A. Basham
*Attorney, Agent, or Firm*—Townsend and Townsend and Crew LLP

[57] ABSTRACT

The present invention identifies a novel, Fas-associated factor 1 termed FAF1 which potentiates Fas-induced cell killing. The invention provides FAF1 nucleic acid and polypeptide compositions as well as methods of using these compositions in the therapeutic treatment of diseases resulting from dysregulation in apoptosis. Also provided are cells carrying and expressing the nucleic acid compositions and methods of using these cells to screen for agonists and antagonists of Fas-mediated apoptosis. Methods of isolating FAF1-interacting proteins are disclosed.

11 Claims, 20 Drawing Sheets

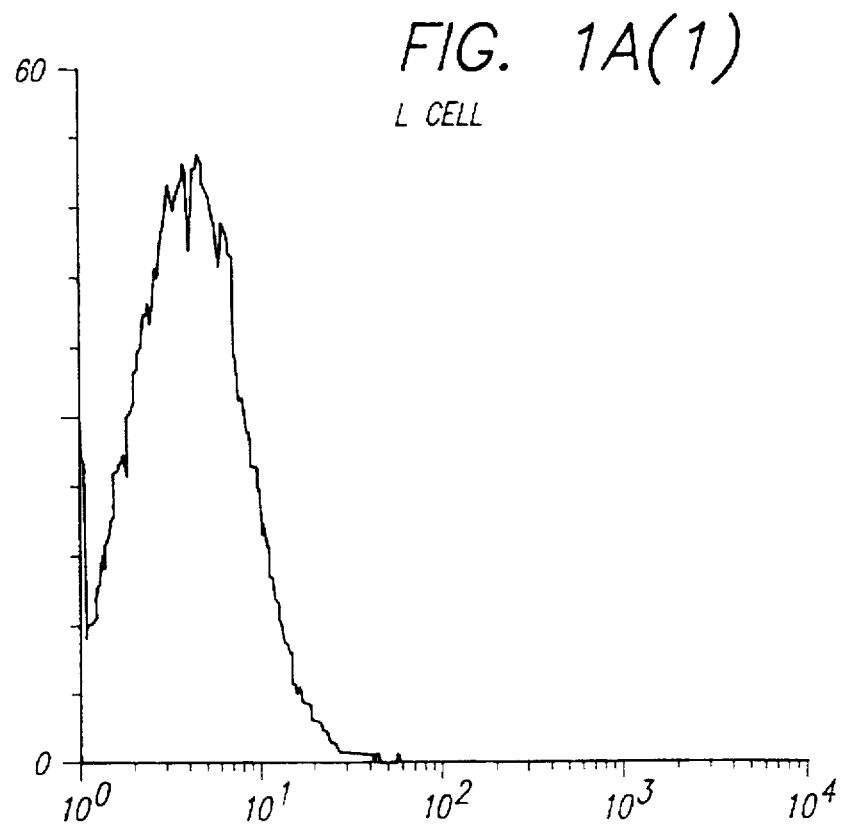
FIG. 1A(1)
L CELL
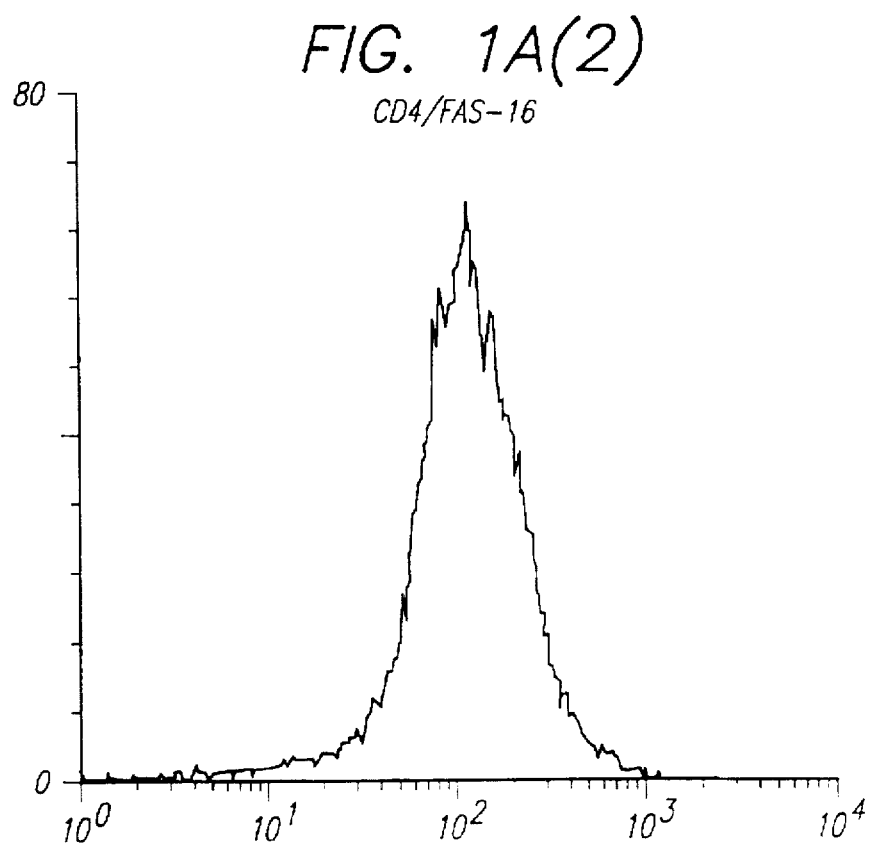
FIG. 1A(2)
CD4/FAS-16

FIG. 1A(3)
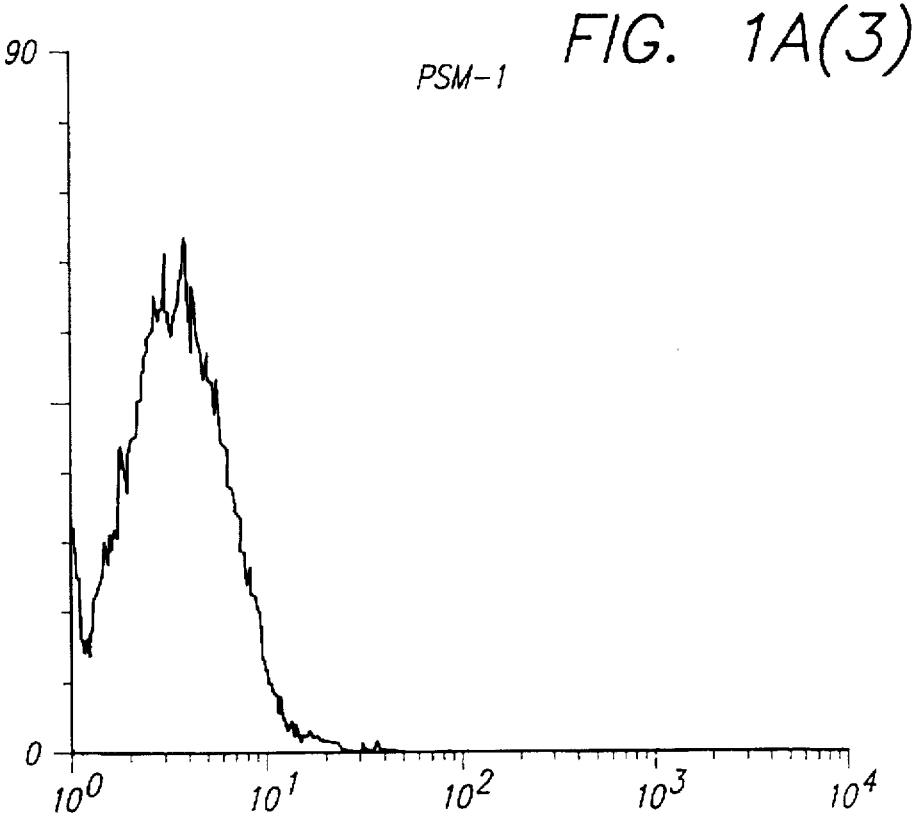
FIG. 1A(4)
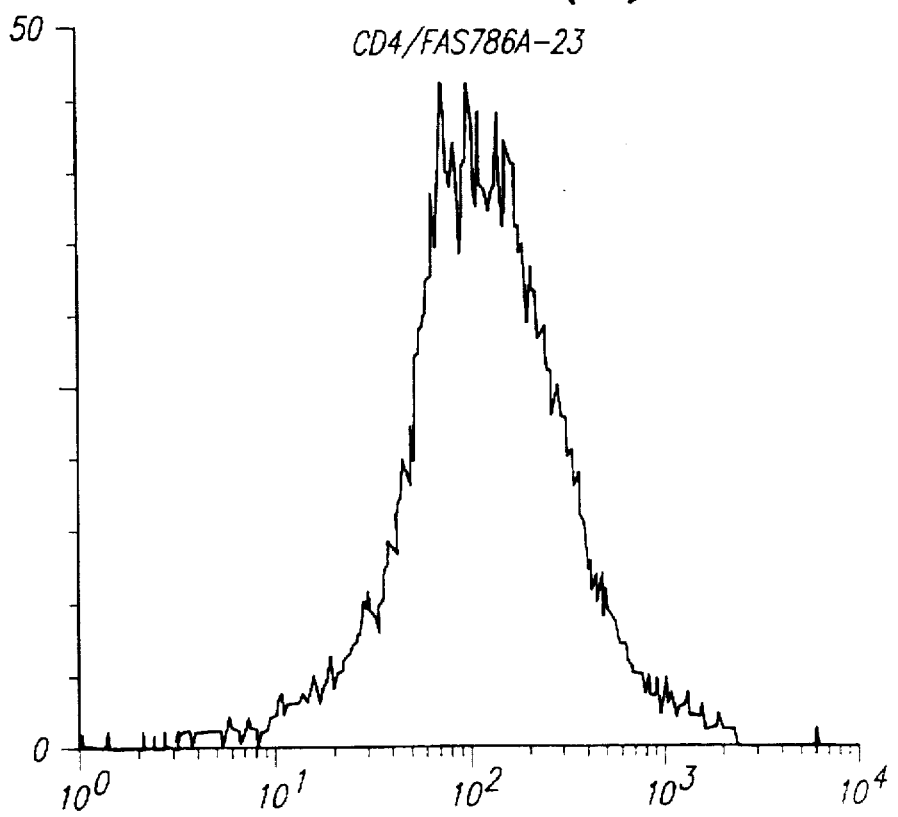

FIG. 1C(A)
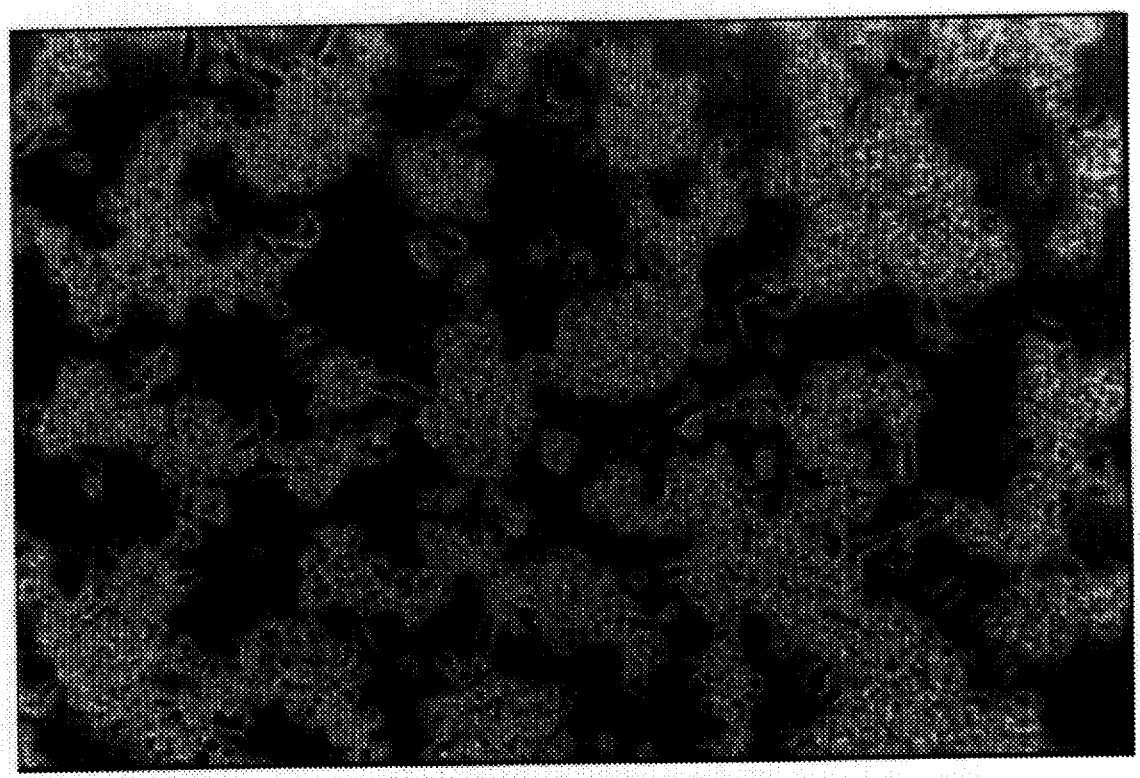
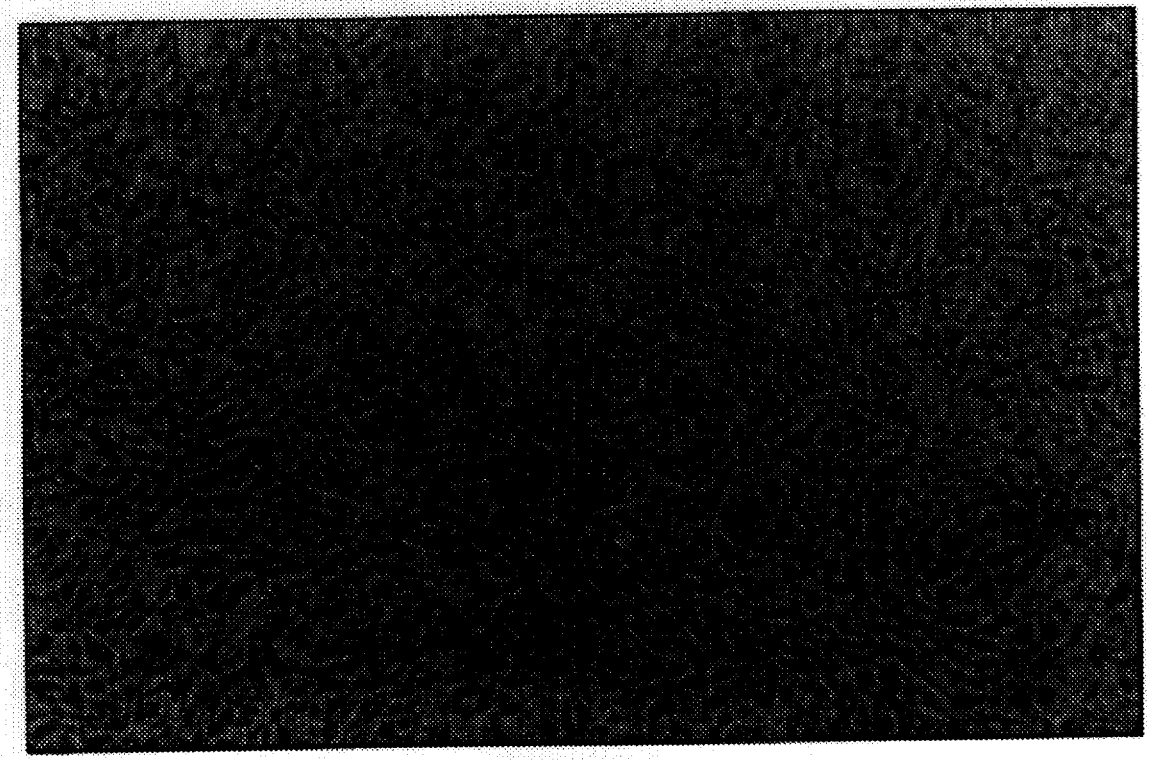
FIG. 1C(B)

FIG. 2A

SEQUENCE RANGE: 1 to 2558

```
           10         20         30         40         50         60
            *          *          *          *          *          *
    TCGAGCTACG TCAGGGCTGG AGGGAGCCGG GCGCGCGCTG TTCGCAACCT GTCCTCCTCC 70         80         90        100        110        120
            *          *          *          *          *          *
    CAGGCGGCGA CGGAAGGACC GGCCCGGCAT CGAGACCAGC CTCCCTCGCA ACCTGTCCTC 130        140        150        160        170        180
            *          *          *          *          *          *
    CTCCCAGGCG GCGACGGAAG GACCGGCCCG GCATCGAGAC CAGCCTCCCC GTCCCGGCAG 190        200        210        220        230        240
            *          *          *          *          *          *
    CTGCGGCGAG GGCTCCGCGG GGCGCAGGCG GGCTCAGGGC GGCTGAAGGT TACCGAGTGC 250        260        270        280        290        300
            *          *          *          *          *          *
    ATGAGCACCT AGTCTCCCGC GCTGCCCCGC CGCCGGTCC  GCCGGCCCCT CCCGCCGGCT 310        320        330        340        350        360
            *          *          *          *          *          *
    CGCCCGCCAG CCCTTCGCCA CCCGGCGGCG GCCGCAGCTT CGGCCGCAGG AGGCGCCGTC 370        380        390        400        410        420
            *          *          *          *          *          *
    TCGCTCCCAG GTGCGCGCTT CGTTCCCGGA GCCGCGGAGC TCGGCGGCCG CCATGGCGTC
                                                             M  A  S 430        440        450        460        470        480
            *          *          *          *          *          *
    CAACATGGAT TTACCGATGA TCCTTGCGGA TTTTCAGGCA TGTACTGGTA TTGAAAACAT
     N  M  D   L  P  M   I  L  A  D   F  Q  A   C  T  G   I  E  N  I 490        500        510        520        530        540
            *          *          *          *          *          *
    CGATGAAGCT ATTACACTGC TTGAGCAAAA TAACTGGGAC TTGGTGGCAG CTATTAATGG
     D  E  A   I  T  L   L  E  Q  N   N  W  D   L  V  A   A  I  N  G
```

FIG. 2A(1)

Sequence: 1 to 2558

```
          550        560        570        580        590        600
           *          *          *          *          *          *
     TGTAATACCA CAGGAAAATG GCATTCTACA AAGTGACTTT GGAGGTGAGA CCATGCCAGG
       V  I  P   Q  E  N    G  I  L  Q   S  D  F   G  G  E    T  M  P  G 610        620        630        640        650        660
           *          *          *          *          *          *
     ACCCACATTT GATCCAGCAA GTCACCCTGC TCCAGCTTCA ACTCCCTCTT CTTCAGCGTT
       P  T  F   D  P  A    S  H  P  A   P  A  S   T  P  S    S  S  A  F 670        680        690        700        710        720
           *          *          *          *          *          *
     TCGACCTGTA ATGCCATCCA GGCAGATTGT AGAAAGGCAG CCTCGAATGC TAGACTTCAG
       R  P  V   M  P  S    R  Q  I  V   E  R  Q   P  R  M    L  D  F  R 730        740        750        760        770        780
           *          *          *          *          *          *
     AGTTGAATAC AGAGACAGAA ATGTTGATGT GGTACTTGAA GACAGCTGTA CTGTTGGAGA
       V  E  Y   R  D  R    N  V  D  V   V  L  E   D  S  C    T  V  G  E 790        800        810        820        830        840
           *          *          *          *          *          *
     GATCAAACAG ATTCTAGAAA ATGAGCTTCA GATACCTGTG CCTAAAATGC TGTTAAAAGG
       I  K  Q   I  L  E    N  E  L  Q   I  P  V   P  K  M    L  L  K  G 850        860        870        880        890        900
           *          *          *          *          *          *
     CTGGAAGACT GGAGACGTGG AAGACAGTAC GGTCTTAAAA TCACTACACT TGCCAAAAAA
       W  K  T   G  D  V    E  D  S  T   V  L  K   S  L  H    L  P  K  N 910        920        930        940        950        960
           *          *          *          *          *          *
     CAACAGTCTT TATGTCCTTA CACCAGACTT GCCACCGCCT TCATCATCCA GCCATGCTGG
       N  S  L   Y  V  L    T  P  D  L   P  P  P   S  S  S    S  H  A  G
```

FIG. 2A(2)

Sequence Range: 1 to 2558

```
           970        980        990       1000       1010       1020
            *          *          *          *          *          *
       TGCCCTGCAG GAATCATTAA ATCAAAACTT CATGCTGATC ATCACCCACC GAGAGGTCCA
        A  L  Q   E  S  L    N  Q  N  F  M  L  I   I  T  H    R  E  V  Q 1030       1040       1050       1060       1070       1080
            *          *          *          *          *          *
       GCGGGAGTAC AACCTGAACT TCTCAGGAAG CAGTACCGTT CAAGAGGTAA AGAGAAATGT
        R  E  Y   N  L  N    F  S  G  S  S  T  V   Q  E  V    K  R  N  V 1090       1100       1110       1120       1130       1140
            *          *          *          *          *          *
       GTATGACCTT ACAAGCATAC CTGTTCGACA TCAGTTATGG GAGGGCTGGC CAGCTTCTGC
        Y  D  L   T  S  I    P  V  R  H  Q  L  W   E  G  W    P  A  S  A 1150       1160       1170       1180       1190       1200
            *          *          *          *          *          *
       CACCGATGAC TCAATGTGTC TTGCTGAATC AGGCCTCTCT TATCCCTGCC ATCGATTAAC
        T  D  D   S  M  C    L  A  E  S  G  L  S   Y  P  C    H  R  L  T 1210       1220       1230       1240       1250       1260
            *          *          *          *          *          *
       TGTGGGAAGA AGAACTTCAC CTGTACAGAC CCGTGAGCAA TCAGAAGAGC AAAGCACGGA
        V  G  R   R  T  S    P  V  Q  T  R  E  Q   S  E  E    Q  S  T  D 1270       1280       1290       1300       1310       1320
            *          *          *          *          *          *
       TGTTCATATG GTTAGTGATA GTGATGGCGA TGACTTTGAA GATGCTTCAG AATTTGGAGT
        V  H  M   V  S  D    S  D  G  D  D  F  E   D  A  S    E  F  G  V 1330       1340       1350       1360       1370       1380
            *          *          *          *          *          *
       GGATGACGGA GAAGTATTTG GCATGGCATC ATCTACCCTG AGAAAATCTC CAATGATGCC
        D  D  G   E  V  F    G  M  A  S  S  T  L   R  K  S    P  M  M  P
```

FIG. 2A(3)

Sequence Range: 1 to 2558

```
            1390       1400       1410       1420       1430       1440
              *          *          *          *          *          *
         AGAAAACGCA GAAAATGAAG GAGATGCCTT ATTACAATTT ACAGCAGAGT TTTCTTCAAG
          E  N  A   E  N  E    G  D  A  L  L  Q  F   T  A  E    F  S  S  R
                    M  K 1450       1460       1470       1480       1490       1500
              *          *          *          *          *          *
         ATATAGTGAC TGCCATCCTG TATTTTATAT TGGCTCATTA GAAGCTGCTT TCCAAGAGGC
          Y  S  D   C  H  P    V  F  Y  I  G  S  L   E  A  A    F  Q  E  A 1510       1520       1530       1540       1550       1560
              *          *          *          *          *          *
         CTTCTATGTG AAAGCCCGAG ACAGAAAACT TCTTGCTATC TACCTCCACC ATGATGAAAG
          F  Y  V   K  A  R    D  R  K  L  L  A  I   Y  L  H    H  D  E  S 1570       1580       1590       1600       1610       1620
              *          *          *          *          *          *
         TGTACTAACC AACGTGTTCT GCTCACAAAT GCTTTGTGCT GAATCCATTG TTTCCTATCT
          V  L  T   N  V  F    C  S  Q  M  L  C  A   E  S  I    V  S  Y  L 1630       1640       1650       1660       1670       1680
              *          *          *          *          *          *
         GAGTCAAAAT TTTATAACCT GGGCTTGGGA TCTGACAAAG GACACCAACA GAGCAAGATT
          S  Q  N   F  I  T    W  A  W  D  L  T  K   D  T  N    R  A  R  F 1690       1700       1710       1720       1730       1740
              *          *          *          *          *          *
         TCTGACAATG TGCAATAGAC ACTTTGGCAG CGTTATTGCA CAAACTATTC GGACTCAAAA
          L  T  M   C  N  R    H  F  G  S  V  I  A   Q  T  I    R  T  Q  K 1750       1760       1770       1780       1790       1800
              *          *          *          *          *          *
         GACAGATCAG TTTCCACTTT TCCTGATTAT CATGGGAAAG CGATCATCTA ATGAAGTGTT
          T  D  Q   F  P  L    F  L  I  I  M  G  K   R  S  S    N  E  V  L
```

FIG. 2A(4)

Sequence Range: 1 to 2558

```
         1810       1820       1830       1840       1850       1860
          *          *          *          *          *          *
      AAATGTGATA CAAGGTAATA CAACAGTGGA TGAGTTAATG ATGAGACTCA TGGCTGCAAT
       N  V  I   Q  G  N    T  T  V  D  E  L  M   M  R  L    M  A  A  M 1870       1880       1890       1900       1910       1920
          *          *          *          *          *          *
      GGAGATTTTC TCAGCTCAA CAACAGGAAGA CATTAAGGAT GAGGATGAAC GTGAAGCCAG
       E  I  F   S  A  Q   Q  Q  E  D  I  K  D    E  D  E    R  E  A  R 1930       1940       1950       1960       1970       1980
          *          *          *          *          *          *
      AGAAAATGTG AAGAGAGAGC AAGATGAGGC CTATCGCCTT TCCCTCGAAG CCGACAGGGC
       E  N  V   K  R  E    Q  D  E  A  Y  R  L   S  L  E    A  D  R  A 1990       2000       2010       2020       2030       2040
          *          *          *          *          *          *
      AAAGAGAGAA GCTCATGAGA GAGAGATGGC AGAACAGTTT CGTTTGGAGC AGATTCGCAA
       K  R  E   A  H  E    R  E  M  A  E  Q  F   R  L  E    Q  I  R  K 2050       2060       2070       2080       2090       2100
          *          *          *          *          *          *
      AGAACAAGAA GAAGAACGTG AGGCCATCAG ACTCTCCTTA GAACAAGCCC TTCCTCCAGA
       E  Q  E   E  E  R    E  A  I  R  L  S  L   E  Q  A    L  P  P  E 2110       2120       2130       2140       2150       2160
          *          *          *          *          *          *
      GCCGAAGGAA GAAAATGCTG AGCCTGTTAG CAAGCTTCGG ATTCGAACCC CCAGTGGCGA
       P  K  E   E  N  A    E  P  V  S  K  L  R   I  R  T    P  S  G  E 2170       2180       2190       2200       2210       2220
          *          *          *          *          *          *
      GTTCCTGGAA CGGCGTTTCC TGGCCAGCAA TAAGCTCCAG ATTGTCTTTG ATTTCGTGGC
       F  L  E   R  R  F    L  A  S  N  K  L  Q   I  V  F    D  F  V  A
```

FIG. 2A(5)

Sequence Range: 1 to 2558

```
         2230       2240       2250       2260       2270       2280
           *          *          *          *          *          *
      TTCCAAGGGA TTTCCATGGG ATGAATTCAA GTTACTGAGC ACCTTTCCTA GGAGAGATGT
       S  K  G    F  P  W    D  E  F  K  L  L  S   T  F  P    R  R  D  V 2290       2300       2310       2320       2330       2340
           *          *          *          *          *          *
      AACTCAGCTA GACCCCAATA AGTCATTATT GGAGGTAAAC TTGTTCCCTC AAGAAACCCT
       T  Q  L    D  P  N    K  S  L  L  E  V  N   L  F  P    Q  E  T  L 2350       2360       2370       2380       2390       2400
           *          *          *          *          *          *
      TTTCCTTCAA GCAAAAGAGT AAACATGACT GAGAGGTGGA AGCAGCCACT CCTGACGAGC
       F  L  Q    A  K  E 2410       2420       2430       2440       2450       2460
           *          *          *          *          *          *
      CAGCGGCACG TGTCAAGAGA TGGGCTCCTC ACCAACCCAC CTACCTGCTC GTGTCACTCA 2470       2480       2490       2500       2510       2520
           *          *          *          *          *          *
      GTTCAATGTC ACACTTCTGC CTCTTGCAA GATTGCTGGAA AAAAGTAATA AACATAGCTA 2530       2540       2550       2560
           *          *          *          *
      CTTAAAAAAA AAAAAAAAAA AACCCTGACG TAGCTCGA
```

FIG. 2B

```
                                                   10                                            20
Met Ala Ser Asn Met Asp Leu Pro Met Ile Leu Ala Asp Phe Gln Ala Cys Thr Gly Ile
                                                   30                                            40
Glu Asn Ile Asp Glu Ala Ile Thr Leu Leu Glu Gln Asn Asn Trp Asp Leu Val Ala Ala
                                                   50                                            60
Ile Asn Gly Val Ile Pro Gln Asn Gly Ile Leu Gln Ser Asp Phe Gly Gly Glu Thr
                                                   70                                            80
Met Pro Gly Pro Thr Phe Asp Pro Ala Ser His Pro Ala Pro Ala Ser Thr Pro Ser Ser
                                                   90                                           100
Ser Ala Phe Arg Pro Val Met Pro Ser Arg Gln Ile Val Glu Arg Gln Pro Arg Met Leu
                                                  110                                           120
Asp Phe Arg Val Glu Tyr Arg Asp Arg Asn Val Asp Val Val Leu Glu Asp Ser Cys Thr
                                                  130                                           140
Val Gly Glu Ile Lys Gln Ile Leu Asn Glu Leu Gln Ile Pro Val Pro Lys Met Leu
                                                  150                                           160
Leu Lys Gly Trp Lys Thr Gly Asp Val Glu Asp Ser Thr Val Leu Lys Ser Leu His Leu
                                                  170                                           180
Pro Lys Asn Asn Ser Leu Tyr Val Leu Thr Pro Asp Leu Pro Pro Pro Ser Ser Ser Ser
```

FIG. 2B(1)

His Ala Gly Ala Leu Gln Glu Ser Leu Asn Gln Asn Phe Met Leu Ile Ile Thr His Arg
190                                                                              200

Glu Val Gln Arg Glu Tyr Asn Leu Asn Phe Ser Gly Ser Ser Thr Val Gln Glu Val Lys
210                                                                              220

Arg Asn Val Tyr Asp Leu Thr Ser Ile Pro Val Arg His Gln Leu Trp Glu Gly Trp Pro
230                                                                              240

Ala Ser Ala Thr Asp Asp Ser Met Cys Leu Ala Glu Ser Gly Leu Ser Tyr Pro Cys His
250                                                                              260

Arg Leu Thr Val Gly Arg Arg Thr Ser Pro Val Gln Thr Arg Glu Gln Ser Glu Glu Gln
270                                                                              280

Ser Thr Asp Val His Met Val Ser Asp Ser Asp Gly Asp Asp Phe Glu Asp Ala Ser Glu
290                                                                              300

Phe Gly Val Asp Asp Gly Glu Val Phe Gly Met Ala Ser Ser Thr Leu Arg Lys Ser Pro
310                                                                              320

Met Met Pro Glu Asn Ala Glu Asn Glu Gly Asp Ala Leu Leu Gln Phe Thr Ala Glu Phe
330                                                                              340

Ser Ser Arg Tyr Ser Asp Cys His Pro Val Phe Tyr Ile Gly Ser Leu Glu Ala Ala Phe
350                                                                              360

FIG. 2B(2)

370
Gln Glu Ala Phe Tyr Val Lys Ala Arg Asp Arg Lys Leu Leu Ala Ile Tyr Leu His His
380

390
Asp Glu Ser Val Leu Thr Asn Val Phe Cys Ser Gln Met Leu Cys Ala Glu Ser Ile Val
400

410
Ser Tyr Leu Ser Gln Asn Phe Ile Thr Trp Ala Trp Asp Leu Thr Lys Asp Thr Asn Arg
420

430
Ala Arg Phe Leu Thr Met Cys Asn Arg His Phe Gly Ser Val Ile Ala Gln Thr Ile Arg
440

450
Thr Gln Lys Thr Asp Gln Phe Pro Leu Ile Ile Met Gly Lys Arg Ser Ser Asn
460

470
Glu Val Leu Asn Val Ile Gln Gly Asn Thr Thr Val Asp Glu Leu Met Met Arg Leu Met
480

490
Ala Ala Met Glu Ile Phe Ser Ala Gln Gln Gln Glu Asp Ile Lys Asp Glu Asp Glu Arg
500

510
Glu Ala Arg Glu Asn Val Lys Arg Glu Gln Gln Asp Glu Ala Tyr Arg Leu Ser Leu Glu Ala
520

530
Asp Arg Ala Lys Arg Glu Ala His Glu Arg Glu Met Ala Glu Gln Phe Arg Leu Glu Gln
540

FIG. 2B(3)

```
         550                          560
Ile Arg Lys Glu Gln Glu Glu Glu Arg Ala Ile Arg Leu Ser Leu Glu Gln Ala Leu
         570                          580
Pro Pro Glu Pro Lys Glu Glu Asn Ala Glu Pro Val Ser Lys Leu Arg Ile Arg Thr Pro
         590                          600
Ser Gly Glu Phe Leu Glu Arg Arg Phe Leu Ala Ser Asn Lys Leu Gln Ile Val Phe Asp
         610                          620
Phe Val Ala Ser Lys Gly Phe Pro Trp Asp Glu Phe Lys Leu Leu Ser Thr Phe Pro Arg
         630                          640
Arg Asp Val Thr Gln Leu Asp Pro Asn Lys Ser Leu Leu Glu Val Asn Leu Phe Pro Gln
         649
Glu Thr Leu Phe Leu Gln Ala Lys Glu
```

PROTEIN, FAF1, WHICH POTENTIATES FAS-MEDIATED APOPTOSIS AND USES THEREOF

This invention was made with Government support under Grant No. HL-32898, awarded by the National Institutes of Health. The Government has certain rights in this invention.

BACKGROUND OF THE INVENTION

Apoptosis or programmed cell death is an important physiological process in multicellular organisms, both during development and for homeostasis. Apoptosis allows the elimination of cells that are no longer necessary, that are produced in excess, that have developed improperly or that have sustained genetic damage. Apoptosis occurs in many different tissue systems and must be properly regulated to maximize benefit to the individual; when the mechanism is dysregulated, it may cause significant disease. Both inhibition of cell death and inappropriate cell death may be deleterious. For example, inhibition of cell death may contribute to disease in the immune system to allow persistence of self-reactive B and T cells, thus promoting autoimmune disease (Watanabe-Fukunaga et al., Nature, 356:314–317 (1992)). Most importantly, cancer may result when cells that fail to die undergo further mutations, leading to a transformed state (Korsmeyer, S. J., Blood, 80:879–886 (1992)).

The protein, Fas, mediates apoptosis. A cell surface receptor, Fas plays an important role in the development and function of the immune system. Malfunction of the Fas system causes lymphoproliferative disorders and accelerates autoimmune diseases. Exacerbation of Fas-mediated apoptosis may cause tissue destruction.

SUMMARY OF THE INVENTION

The present invention provides the identification and isolation of a novel Fas-associated factor 1, termed FAF1, and the FAF1-encoding DNA. As a cytoplasmic protein, FAF1 was shown herein to bind to the wild type but not the inactive point mutant of Fas. FAF1 specifically interacts with the cytoplasmic domain of wild type Fas and potentiates Fas-induced cell killing. FAF1 is a signal transducing molecule in the regulation of apoptosis.

The FAF1 nucleic acids and polypeptides find many uses. It would be desirable to be able to control apoptosis by enhancing or decreasing the susceptibility of individual cell types to undergo apoptosis, especially when dysregulation of the process leads to disease. In particular, it would be desirable to provide therapeutic intervention in disease conditions where apoptosis is dysregulated due to Fas or FAF1 malfunction. Blockage or activation of FAF1 function in apoptosis can be used for example, in the treatment of cancer, immune disorders such as autoimmune diseases, infectious diseases, and myocardial infarction and neuronal infarction in cardiovascular diseases. Heretofore, such therapeutic approaches involving FAF1 were not possible. The present discovery of FAF1 fulfills these and other needs.

The present invention provides the nucleotide and amino acid sequence of FAF1 as well as polypeptide and nucleic acid compositions based on FAF1. The uses and methods of use of the FAF1 nucleic acid and polypeptide compositions are disclosed.

One aspect of this invention is to provide an isolated nucleic acid comprising at least 85% sequence identity with the nucleotide sequence of SEQ ID NO:1, an allelic or species variation thereof, or a fragment thereof. A nucleic acid comprising the nucleotide sequence of SEQ ID NO:1 is provided. Also provided is a recombinant DNA molecule comprising the nucleotide sequence of SEQ ID NO:1 or a fragment thereof. In one embodiment, the recombinant DNA molecule encodes a FAF1-GAL4 transactivation domain fusion protein. A cell is provided which contains the recombinant DNA molecule comprising the nucleotide sequence of SEQ ID NO:1 or a fragment thereof.

Another aspect of the invention is to provide an isolated polypeptide comprising at least 85% sequence identity with the sequence of SEQ ID NO:2, an allelic or species variation thereof, or a fragment thereof. The polypeptide can be provided in a kit. The polypeptide may further comprise an influenza virus HA epitope tag. An isolated polypeptide comprising the sequence of SEQ ID NO:2 is also provided. In a specific embodiment, the polypeptide is one capable of associating with the cytoplasmic domain of Fas.

Yet another aspect of the invention is to provide an isolated polypeptide comprising the sequence of SEQ ID NO:2, an allelic or species variation thereof, or a fragment thereof, wherein the isolated polypeptide is a fusion protein. A FAF1-GAL4 activation domain fusion protein is specifically provided. In one aspect, the fusion protein comprises a tag, or a product of a second gene or fragment of that second gene product. A fusion protein is provided wherein the tag is GST, an epitope tag or an enzyme or wherein the second gene is lacZ.

A different aspect of the invention is the provision of antibodies that specifically bind a polypeptide comprising the sequence of SEQ ID NO:2, an allelic or species variation thereof, or a fragment thereof. These antibodies can be polyclonal, such as the rabbit antiserum provided herein, or monoclonal. A hybridoma capable of producing a monoclonal antibody to a FAF1 polypeptide is provided. Also provided is a kit comprising any antibody preparation to the above-mentioned polypeptides.

In another aspect of the invention, a method is provided for isolating a FAF1 gene or fragment thereof, comprising screening a DNA library using a FAF1 probe to identify a hybridizing clone and isolating said FAF1 gene or gene fragment from said hybridizing clone. A FAF1 probe suitable for use in this method is one which comprises the nucleotide sequence of SEQ ID NO:1 or a fragment thereof. The method is useful to isolate a human FAF1 gene as well as FAF1 genes from other species.

Another aspect of the invention is to provide a method of modulating or blocking Fas activity comprising providing a Fas-interacting domain polypeptide of FAF1 in a cell expressing Fas protein wherein said Fas-interacting domain polypeptide of FAF1 binds to said Fas protein to block Fas activity. In one embodiment, the Fas-interacting domain polypeptide of FAF1 is provided by introducing an expression vector encoding a Fas-interacting domain polypeptide of FAF1 into the Fas expressing cell. A method of activating FAF1-mediated apoptosis in a cell is disclosed, the method comprising providing a constitutively active FAF1 to the cell.

An important aspect of the invention is a method of screening for an agonist or an antagonist of FAF1, comprising contacting a cell expressing both Fas and FAF1 with a test molecule, activating Fas, and analyzing the cell for any effects on apoptosis, increased apoptosis indicative that the test molecule is an agonist and decreased or loss of apoptosis indicative that the test molecule is an antagonist. The test molecules can be peptides, oligonucleotides, lipids, toxins, hormones, small proteins, drugs and compounds from plant or animal sources and recombinantly produced substances. In a specific embodiment, peptide libraries are screened.

The cells are analyzed for effects on apoptosis such as cell membrane blebbing and/or DNA fragmentation. Fas is activated by binding to Fas ligand or crosslinking with antibodies. Fas and/or FAF1 can be expressed as a fusion protein. In a particular embodiment, the cell expresses CD4/fas and HA epitope tagged FAF1 fusion proteins. An L cell expressing both these fusion proteins is specifically provided in the invention.

The invention further provides a pharmaceutical composition useful in the treatment of a disease resulting from dysregulated apoptosis, comprising a FAF1 polypeptide and a pharmaceutically acceptable carrier. Instead of the FAF1 polypeptide, the pharmaceutical composition can comprise an expression vector capable of expressing the FAF1 polypeptide in an affected cell. The diseases contemplated for such treatment include cancer, autoimmune disease and viral infections. For these diseases, a constitutively active FAF1 polypeptide can be provided in the pharmaceutical composition. In a different set of diseases comprising myocardial infarction, stroke and reperfusion injury, arrest or blockage of apoptotic cell death is targeted. In the latter set of disease conditions, it may be therapeutically effective to express a Fas-interacting domain polypeptide in the affected cell to block the interaction between endogenous Fas and FAF1, thus blocking FAF1-potentiated apoptosis. Also provided are methods of alleviating a patient suffering from the aforementioned diseases by administering to the patient, a therapeutically effective amount of the above pharmaceutical compositions.

Finally, the invention provides several methods of isolating a FAF1-interacting protein. One method requires contacting a cell lysate suspected of containing a FAF1-interacting protein with a FAF1 polypeptide and isolating any protein bound to the FAF1 polypeptide, as a FAF1-interacting protein. A second method comprises labeling the cellular proteins, activating Fas expressed on the cell, immunoprecipitating FAF1 from the cell lysate and identifying a labeled protein that coimmunoprecipitates with FAF1. In a third method, a peptide library is exposed to a FAF1 protein to allow one or more peptides to bind to the FAF1 protein. Any bound peptide will be isolated as a FAF1-interacting protein.

BRIEF DESCRIPTION OF THE DRAWINGS

FIG. 1A shows surface expression of CD4/fas and CD4/fas786A detected by fluorescent activated cytometry scanning (FACS) analysis.

FIG. 1C shows the morphology of cells after anti-CD4 crosslinking. Cells were crosslinked as described as in FIG. 1B and photographs were taken ten hours later. Top panel (A) shows CD4/fas-16 cells, bottom panel (B) shows CD4/fas786A-23 cells.

FIG. 2A shows the nucleotide sequence (SEQ ID NO:1) of the cDNA encoding FAF1.

FIG. 2B is an amino acid sequence (SEQ ID NO:2) deduced from the nucleotide sequence of the FAF1 cDNA.

In FIG. 3A–C, the lanes are as follows: Cos cells were transfected with PSM plus PCGN8.1 (lane 1), PSMCD4/fas plus PCGN (lane 2), PSMCD4/fas plus PCGN8.1 (lane 3) or PSMCD4/fas786A plus PCGN8.1 (lane 4).

FIG. 3B shows a Western blot analysis blotting with 12CA5 antibody after immunoprecipitation of CD4.

FIG. 3C shows immunoprecipitated chimeric molecules of CD4/fas or CD4/fas786A detected by Western blot. The blot from FIG. 3B was re-probed with anti-CD4 serum (a gift of Dr. D. R. Littman).

DESCRIPTION OF THE PREFERRED EMBODIMENT

Figure 1B:
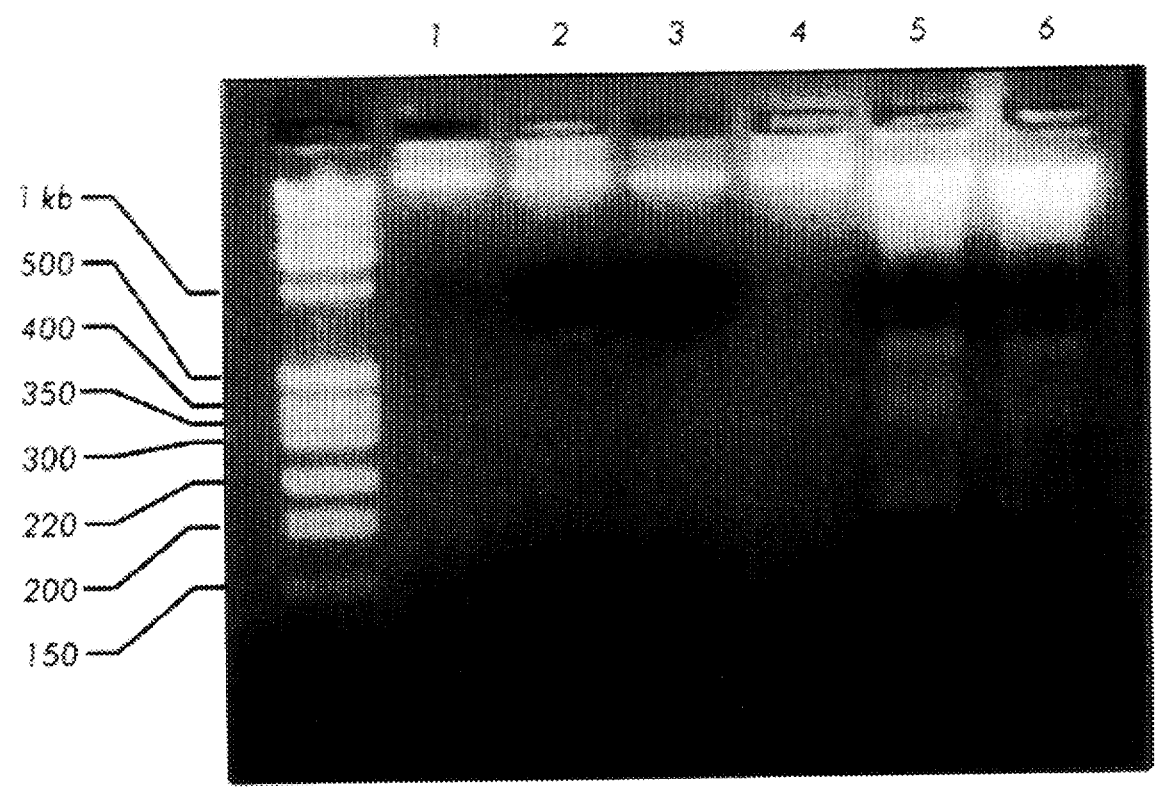
FIG. 1B shows fragmentation of DNA from CD4/fas786A-23 cells (lanes 1–3) and from CD4/fas-16 cells (lanes 4–6) after anti-CD4 crosslinking. Lanes 1 and 4 show DNA from control cells incubated with actinomycin D (0.5 ng/ml) only. Lanes 2 and 5 show DNA from cells crosslinked with L3T4 Rat anti-CD4 (GK1.5) (1 µg/ml) alone. Lanes 3 and 6 show DNA from cells incubated with both L3T4 (1 µg/ml) and anti-Rat IgG (0.5 µg/ml of Rabbit anti-Rat IgG, Zymed).

Fas antigen, a member of TNF/NGF (Tumor Necrosis Factor/Nerve Growth Factor) receptor family, is a cell surface protein that mediates apoptosis. Fas induces apoptosis when activated by Fas ligand (FasL) binding or anti-Fas antibody crosslinking (Nagata, S., Seminars in Immunol., 6:3–8 (1994)). Fas plays an important role in the development and function of the immune system (Nagata, supra, Lowin et al., Nature, 370:650–652 (1994)). Malfunction of the Fas system causes lymphoproliferative disorders and accelerates autoimmune diseases, whereas exacerbation of Fas activity causes tissue destruction.

A point mutation in the cytoplasmic domain of Fas (a single base pair change from T to A at base number 786), replacing isoleucine with asparagine, abolishes the apoptotic signal transducing property of Fas (Watanabe-Fukunaga et al., Nature, 356:314–317 (1992)). Mice homozygous for this mutant allele (lpr$^{cg}$/lpr$^{cg}$ mice) develop lymphadenopathy and an autoimmune disease that resembles human systemic lupus erythematosus (Watanabe-Fukunaga, supra). They produce large quantities of IgG and IgM including autoantibodies such as anti-DNA, and rheumatoid factor (Cohen et al., Annu. Rev. Immunol., 9:243 (1991)) and develop nephritis or arthritis. Patients have been described with phenotypes similar to that of lpr mice (Sneller et al., J. Clin. Invest., 90:334 (1992)) and patients with altered Fas were recently reported (Rieux-Laucat et al., Abstracts of the 12th European Immunology Meeting, Barcelona (European Federation of Immunological Societies) (June 1994)).

The present invention identifies a novel Fas-associated factor 1, termed FAF1. FAF1, which was isolated using the two-hybrid screen in yeast (Durfee et al., *Genes Dev.*, 7:555–569 (1993), specifically interacts with the cytoplasmic domain of wild type Fas but not the lpr$^{cg}$ mutated Fas protein. This interaction occurs not only in yeast but also in mammalian cells. When expressed in L cells, FAF1 potentiated Fas-induced apoptosis. A search of available DNA and protein sequence data banks did not reveal any significant homology between FAF1 and other known proteins. Therefore, FAF1 is a novel protein that binds to the wild type but not the inactive point mutant of Fas; it potentiates Fas-induced cell killing and is a signal transducing molecule in the regulation of apoptosis.

Blockage or activation of FAF1 function in apoptosis can be used in the treatment of diseases including cancer, immune disorders such as autoimmune diseases, infectious diseases, and myocardial infarction and neuronal infarction in cardiovascular diseases.

Characterization of Apoptosis

The characteristics of cell death by apoptosis include cytoplasmic and nuclear condensation, loss of membrane integrity and extensive fragmentation of chromosomal DNA. The degraded DNA from apoptotic cells forms a characteristic ladder when analyzed by gel electrophoresis (Vaux, D., *Proc. Natl. Acad. Sci.*, 90:786–789 (1993)).

Yeast Two Hybrid Screening

The yeast two-hybrid system (Durfee et al., *Genes Dev.*, 7:555–569 (1993)) can be utilized to detect proteins capable of interacting with a known protein. Briefly, the method is as follows. Plasmids are constructed to encode two hybrid proteins which are coexpressed in *Saccharomyces cerevisiae*. One hybrid consists of the DNA-binding domain of the yeast transcriptional activator protein GAL4, fused to the known protein; the other hybrid consists of the GAL4 activation domain fused to protein sequences encoded by a library of DNA fragments. Interaction between the known protein and a protein encoded by one of the library plasmids leads to transcriptional activation of a reporter gene containing a binding site for GAL4. A suitable reporter gene is the *Saccharomyces cerevisiae* HIS3 gene and the *E. coli* lacZ gene (encoding β-galactosidase (β-gal)). Yeast cells are tested for growth in media lacking histidine and for expression of β-gal activity which can be assayed by detecting blue colonies on a plate containing the substrate 5-bromo-4-chloro-3-indolyl β-galactoside.

In the present invention, the hybrid construct encoding the known protein consists of the λ repressor dimerization domain/Fas cytoplasmic domain chimera fused to the DNA-binding domain of GAL4. Using this two-hybrid screening system, cDNA clones encoding a protein that interacted with the Fas fusion molecule were isolated. A probe prepared from the longer cDNA clone was used to screen a murine thymus cDNA library from which two full length cDNA clones encoding FAF1 were isolated.

Definitions

As used herein, a "Fas-associated factor 1" is a protein which has an affinity for Fas and binds or physically interacts with Fas.

A "FAF1 interacting molecule" or "FAF1 associating molecule" is a molecule which has an affinity for FAF1 and binds or physically interacts with FAF1. If the interacting molecule is a protein, it is referred to herein as "FAF1 interacting protein". The interaction can be transient, lasting only a fraction of a second or it can be stable so as to enable the detection of the complex of FAF1-FAF1 interacting molecule. Preferably, this interaction persists for at least ten seconds, ideally several minutes. The term "FAF1 interacting molecule" does not imply any particular molecular size or other structural or compositional feature other than that the molecule or compound in question is capable of binding or otherwise interacting with FAF1. The interacting molecule may be a substrate of FAF1, an enzyme that acts on FAF1, a protein that FAF1 is involved in localizing, an effector molecule of FAF1 and/or Fas or a molecule that alters the conformation of FAF1 upon interaction. Interacting or associating molecules that can be investigated by this invention include but are not restricted to agonists and antagonists of FAF1, cellular proteins encoded by oncogenes or proto-oncogenes, lipids, toxins, hormones, sugars, cofactors, peptides, proteins, enzyme substrates, drugs and compounds from plant or animal sources.

A "Fas-interacting domain polypeptide or peptide of FAF1" is defined as a polypeptide or peptide having a sequence corresponding to a region in the wild-type FAF1 protein, which physically interacts with the cytoplasmic region of Fas. The peptide will typically be in the range of 10–30, preferably 25, amino acids.

An "isolated nucleic acid" is a nucleic acid, e.g., an RNA, DNA, or a mixed polymer, which is substantially separated from other genome DNA sequences as well as proteins or complexes such as ribosomes and polymerases, which naturally accompany a native sequence. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule. An "isolated polypeptide" or protein carries a similar meaning with the polypeptide or protein being substantially separated from any cellular contaminants and components naturally associated with the protein in vivo.

An "allelic variation" in the context of a nucleic acid or a gene is an alternative form (allele) of a gene that exists in more than one form in the population. At the polypeptide level, "allelic variants" generally differ from one another by only one, or at most, a few amino acid substitutions. A "species variation" of a nucleic acid or a polypeptide is one in which the variation is naturally occurring among different species of an organism.

A "fragment" of a nucleic acid is a stretch of at least about 18 nucleotides, more typically at least about 50 to 200 nucleotides but less than 2 kb. A polypeptide "fragment" or "segment" is a stretch of amino acid residues of at least about 6 contiguous amino acids from a particular sequence, more typically at least about 12 amino acids but can be up to 20 amino acids.

The term "recombinant" or "recombinant DNA molecule" refers to a nucleic acid sequence which is not naturally occurring, or is made by the artificial combination of two otherwise separated segments of sequence. By "recombinantly produced" is meant artificial combination often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. "Recombinant DNA molecules" include cloning and expression vectors.

Two nucleic acids share sequence "identity" or "homology" if the two nucleic acids or designated segments thereof, when optimally aligned with appropriate nucleotide insertions or deletions, are identical in at least about 50% of the nucleotides. "Substantial homology" in the nucleic acid context means that the nucleic acids or their complementary strands, when compared, are identical when optimally aligned with appropriate nucleotide insertions or deletions, in at least about 60% of the nucleotides, usually at least about 70%, more usually at least about 80%, preferably at least about 90%, and more preferably at least about 95 to 98% of the nucleotides. Alternatively, substantial homology exists when the segments will hybridize under selective hybridization conditions, to a strand, or its complement, using a sequence derived from the FAF1 nucleic acids. Selectivity of hybridization exists when hybridization occurs with a certain degree of specificity rather than being random. Typically, selective hybridization will occur when there is at least about 55% homology over a stretch of at least about 14 nucleotides, preferably at least about 65%, more preferably at least about 75%, and most preferably at least about 90%. See, Kanehisa, *Nuc. Acids Res.*, 12:203–213 (1984).

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands on the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See, generally, Mullis et al., *Cold Spring Harbor Symp. Quant. Biol.*, 51:263 (1987); Erlich, ed., *PCR Technology*, (Stockton Press, N.Y., 1989). As used herein, PCR is considered to be one, but not the only, example of a nucleic acid polymerase reaction method for amplifying a nucleic acid test sample, comprising the use of a known nucleic acid (DNA or RNA) as a primer.

"Operably Linked" means that a polynucleotide sequence it is placed into a functional relationship with another polynucleotide sequence. For example, a promoter is operably linked to a coding sequence if it acts in cis to modulate the transcription of the linked sequence. Generally, "operably linked" means that the DNA sequences being linked are contiguous and in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

A "primer" or "oligonucleotide" can be a single-stranded polynucleotide that may be chemically synthesized by known methods. Suitable oligonucleotides may be prepared by the phosphoramidite method described by Beaucage and Carruthers, *Tetr. Lett.*, 22:1859 (1981), or by the triester method, according to Matteucci et al., *J. Am. Chem. Soc.*, 103:3185 (1981), or by other methods such as by using commercial automated oligonucleotide synthesizers such as Applied Bio Systems oligonucleotide synthesizer, according to the specifications provided by the manufacturer.

"Epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

As used herein, "constitutively active FAF1" means that FAF1 is functionally active independent of prior activation of Fas. Cells expressing the constitutively active FAF1 will exhibit induced apoptosis without prior activation of Fas by Fas ligand binding or Fas cross-linking. "Constitutively active FAF1" shall be deemed to include functional derivatives thereof or homologs thereof of the wild-type FAF1 protein. Derivatives can be produced by modifying any region in the wild-type protein such as by deleting negative regulatory regions or by making amino acid substitutions.

Generally, the nomenclature used hereafter and the laboratory procedures in cell culture, molecular genetics, and nucleic acid chemistry described below are those well known and commonly employed in the art. Standard techniques such as described in Sambrook et al., *Molecular Cloning, A Laboratory Manual*, 2nd edition, Cold Spring Harbor Laboratory, Cold Spring Harbor, N.Y. (1989), are used for recombinant nucleic acid methods, nucleic acid synthesis, cell culture, and transgene incorporation, e.g., electroporation, injection, lipofection. Generally enzymatic reactions, oligonucleotide synthesis, and purification steps are performed according to the specifications. The techniques and procedures are generally performed according to conventional methods in the art and various general references which are provided throughout this document. The procedures therein are believed to be well known in the art and are provided for the convenience of the reader.

Specific Embodiments
Nucleic Acid and Polypeptide Compositions

The present invention provides an "isolated nucleic acid" encoding a novel Fas-associated factor 1, defined herein as FAF1. The nucleotide sequence of the cDNA encoding full length FAF1, SEQ ID NO:1, is shown in FIG. 2A and the amino acid sequence, SEQ ID NO:2, is shown in FIG. 2B.

Specifically provided by the invention is a nucleic acid comprising at least 85% sequence identity, preferably 90%, most preferably 95% to 98% sequence identity with the nucleotide sequence of SEQ ID NO:1, an "allelic or species variation" thereof, or a fragment thereof. The nucleic acid compositions of the present invention, whether RNA, cDNA, genomic DNA or a hybrid of the various combinations, can be isolated from natural sources or may be synthesized in vitro.

The invention also provides certain recombinant DNA molecules comprising the nucleotide sequence of SEQ ID NO:1 or a fragment thereof, such as the expression construct PCGN8.1 encoding FAF1 tagged at the N-terminus with the HA epitope, and the FAF1/GAL4 transactivation domain fusion construct.

Compositions of the FAF1 polypeptide and derivatives thereof are also provided. These compositions will be full length natural forms, the natural forms including allelic and species variations of the polypeptide encoded by SEQ ID NO:1, fragments of the natural forms, fusion proteins with those fragments and modified forms of each. Fusion proteins based on the FAF1 sequence include the HA epitope-tagged FAF1 and the FAF1/GAL4 fusion protein used in the yeast two-hybrid system described in the experimental examples. FAF1 polypeptides will generally be synthesized by expression from recombinant DNA molecules. Alternatively, FAF1 fragments and peptides can be synthesized by chemical methods such as described in Merrifield. B., *Science*, 232:342 (1986); Kent. S. B. H.. *Ann. Rev. Biochem.*, 57:957 (1988); Offord, R. E., *Semisynthetic Proteins*, Wiley Publishing (1980); and Atherton et al.. *Solid Phase Peptide Synthesis, A Practical Approach,*, Oxford University Press, Oxford (1989).

In a preferred embodiment, the FAF1 polypeptide or fragment thereof is capable of associating with the cytoplasmic domain of Fas. In addition, pharmaceutical compositions are provided that include the FAF1 polypeptide and its derivatives with a pharmaceutically acceptable carrier.

Uses of FAF1 Nucleic Acids

The FAF1 nucleic acid and fragments thereof have various uses. In one aspect of the invention, the mouse full length FAF1 nucleic acid according to the sequence of SEQ ID NO:1, or fragments thereof, are used to prepare probes to screen DNA libraries to isolate FAF1 genes or gene fragments encoded by other species, particularly human. The methods of screening DNA libraries are generally well known, see, e.g., Sambrook et al. (1989). If less than the full length FAF1 sequence is used, the probes will be oligonucleotides or DNA fragments having at least about 25 nucleotides, more usually at least about 100 nucleotides, and fewer than about 2 knt (kilonucleotides), usually fewer than about 0.5 knt. Preferably, the probe should be free of vector sequences. The probes are typically prepared labeled. Radiolabels such as $^{32}P$ are normally used although non-radioactive labels are also suitable.

Conditions for hybridization can be varied. Initially, less stringent conditions can be used. However, if a high background of non-specific hybridization is observed, more stringent conditions will be employed.

The screening of mammalian cDNA or genomic DNA libraries, especially human DNA libraries, can be targeted although eukaryotes such as yeast and insects are also of interest for evolutionary comparisons. The DNA libraries may be constructed in phage, bacteria or yeast. Clones that hybridize to the probe are identified such as by autoradiography if radiolabeled probes are used. DNA is isolated from hybridizing clones and analyzed for the presence of FAF1 gene sequences as verification that the hybridizing clone carries all or part of the FAF1 gene. The DNA sequence carried by the clone is compared with that of SEQ ID NO:1. The FAF1 gene or fragment thereof will then be isolated from the vector by restriction endonucleases. It may be necessary to isolate several overlapping DNA sequences from different hybridizing clones to recombinantly reproduce the full length gene in one contiguous DNA fragment.

Alternatively, with the availability of the mouse FAF1 sequence, FAF1 genes from other species can be isolated by Polymerase Chain Reaction (PCR) by selecting appropriate pairs of primers based on the known sequence and using genomic DNA or cDNA prepared from cells as the template. Primers can be chemically synthesized and will be at least 10 nucleotides in length, more usually 14 nucleotides, preferably 17 nucleotides, but can be as long as 100 bp nucleotides. Pairs of primers corresponding to the 5' and 3' ends of the gene or to the internal regions of the gene can be used. Several rounds of PCR may be required to prepare overlapping clones that can then be linked by recombinant methods to produce the entire gene in one DNA fragment.

A gene that hybridizes with the probe and is determined to be substantially homologous to the FAF1 gene in nucleotide sequence will be isolated. The homologous gene will be inserted into an appropriate expression vector and introduced into a suitable host for expression to produce the encoded polypeptide. The encoded polypeptide will then be assayed to determine if it associates with the appropriate species of Fas and functions like mouse FAF1, using the same procedure for analyzing the interaction of FAF1 with Fas, described below in the Experimental Examples.

Other FAF1 structurally- or functionally-related family member proteins will associate and interact with receptors similar to Fas and regulate apoptosis in other systems. The same library screening approach can also be used to identify other members of the family that share "substantial homology" with FAF1.

The FAF1 probes can also be used to determine whether RNA encoding FAF1 or a FAF1 homolog is present in a cell. This can be done by the procedure of Northern Blotting. In situ hybridization can also be performed on tissue sections of the organism to determine developmental regulation and compare expression levels in various tissues. The probes can be labeled using any suitable labels or tags. e.g., radiolabel, biotin-avidin. The procedures of preparing probes, Southern blotting, Northern blotting and in situ hybridizations are well known in the art. See, for example, Sambrook et al., 1989.

The invention also provides a method of determining if the FAF1 gene from a cell of interest is mutated. The cells can be from cultured cell lines or from tissue isolated from an animal or human. For example, cells can be prepared from a human tumor biopsy. PCR can be used to amplify all or part of the FAF1 gene using selected primers and the amplified DNA fragment sequenced or analyzed for restriction enzyme cleavage patterns. The nucleotide sequence or restriction analysis is compared to the wild type sequence of FAF1 from the appropriate species. Therefore, the wild type sequence acts as a standard or positive control.

Another aspect of the invention is the mapping of the functional domains of FAF1. Functional domains of FAF1 include regions of FAF1 that: interact with Fas; interact with effector molecules; exhibit an enzymatic activity; or regulate the activity of FAF1 itself. Manipulating these domains of FAF1 can provide a means by which to control Fas and FAF1 mediated apoptosis. For example, polypeptides or peptides corresponding to the Fas-interacting domain of FAF1 can be used to block Fas mediated apoptosis. Such polypeptides will generally be in the range of 6 to 100 amino acids. Circumstances whereby blocking of apoptotic cell death is desirable are described below under therapeutic uses.

There may be negative regulatory regions in FAF1 that control the activation of FAF1 so that premature or unnecessary cell death does not occur. These regulatory regions also serve as useful targets for mutagenesis to affect the Fas apoptotic signaling pathway. For example, a constitutively active FAF1 could be produced by removing a negative regulatory region. Such a modified FAF1 can be selectively expressed in targeted population of cells to affect cell death. This approach can be used to target elimination of cells that exhibit uncontrolled proliferation such as cancerous cells and autoreactive cells.

The method of mapping functional domains can be accomplished by generating a series of FAF1 deletion mutants which can then be compared to the wild-type FAF1 in biological function. The deletion mutants will be produced recombinantly using the full length FAF1 nucleic acid as starting material, and more conveniently, the HA-epitope tagged FAF1 described in the Experimental Examples. Tagging the mutant FAF1 molecules either using the HA epitope or some other tag is desirable to facilitate detection of the mutant and to distinguish the transfected from the endogenous FAF1.

Generally, the mutants will have overlapping deletions. Initially, mutants will be created that have deletions typically in the range of 10–50 amino acids. For subsequent more precise mapping, the deletions in a particular region will be smaller, typically in the range of 5–10 amino acids. Mutants having single amino acid changes will be useful to define key residues that determine structure or that may be involved in physical contact with Fas or a downstream interacting or effector molecule of FAF1. Such mutants can be generated by known techniques such as by site-directed mutagenesis or by PCR.

Each deletion mutant is then transfected into an appropriate host cell and the affects of each deletion on the function of FAF1, assessed. To facilitate analysis of the transfected FAF1, the host cell preferably expresses little or no endogenous FAF1 or expresses a mutated endogenous FAF1 that is non-functional. Preferably, mammalian cell lines amenable to transfection will be used and these include Cos and L cells.

The mutant transfected FAF1 will be analyzed for various characteristics that indicate increased, reduction or complete loss of Fas-mediated function. For example, mutant FAF1 will be analyzed for physical association with Fas by its ability to coimmunoprecipitate with Fas or a Fas fusion polypeptide. The extent to which mutant FAF1 can potentiate Fas-mediated apoptosis will be quantitated. Such assays are described in more detail under Experimental Examples below.

The invention provides FAF1 nucleic acid and fragments thereof to prepare expression constructs for FAF1 and FAF1 polypeptide fragments. The expression vectors will contain the necessary elements for transcription and translation of the DNA fragments into polypeptide if these elements are not already present in the DNA fragments themselves. These necessary elements include a promoter 5' of the DNA insert to be expressed, a transcription and translation initiation site, stop codons, poly-A signal sequence, splice signals. DNA sequences encoding the protein will be operably linked to a promoter appropriate for expression in a particular cell type. Usually a strong promoter will be employed to provide for high level transcription and expression. Examples of strong promoters include human cytomegalovirus promoter. An enhancer may be necessary to function in conjunction with the promoter. The expression construct normally comprises one or more DNA sequences encoding FAF1 under the transcriptional control of a native or other promoter. Usually the promoter will be a eukaryotic promoter for expression in a mammalian cell, where the mammalian cell may or may not result in the expression of FAF1. The selection of an appropriate promoter will depend upon the host, but promoters such as the human cytomegalovirus promoter, viral LTRs such as SFFV LTR, and prokaryotic promoters such as trp, lac and phage promoters, tRNA promoters and glycolytic enzyme promoters are known. In some circumstances, an inducible promoter may be preferred. See, e.g., Sambrook et al., *Molecular Cloning: A Laboratory Guide*, Vols. 1–3 (1989), Cold Spring Harbor Press.

Plasmid, viral or YAC vectors are contemplated. Conveniently available expression vectors which include the replication system and transcriptional and translational regulatory sequences together with polylinker restriction sites for insertion of the protein encoding sequence, may be employed. Such expression vectors are commercially available such as from Stratagene, Inc. Examples of workable combinations of cell lines and expression vectors are described in Sambrook et al. (1989); see also, Metzger et al., *Nature*, 334:31–36 (1988).

It may be desirable to produce the FAF1 protein or fragments thereof in a prokaryotic host, in which case a prokaryotic promoter is preferred. Examples of prokaryotic promoters are trp, lac, and lambda. See Sambrook et al. (1989) for other useful prokaryotic promoters. Usually a strong promoter will be employed to provide for high level transcription and expression.

The expression construct will often be contained in a vector capable of stable extrachromosomal maintenance in an appropriate cellular host or may be integrated into the host genome. The expression construct may be bordered by sequences which allow for insertion into a host, such as transposon sequences, lysogenic viral sequences, or the like. Normally, markers are provided with the expression construct which allow for selection of host cells containing the construct. The marker is preferably on the same DNA molecule but can be on a different DNA molecule that is cointroduced into the host cell. In prokaryotic cells, markers such as a resistance to a cytotoxic agent, complementation of an auxotrophic host to prototrophy, production of a detectable product, etc., serve the purpose.

The expression construct can be joined to a replication system recognized by the intended host cell. Various replication systems include viral replication systems such as retroviruses, simian virus, bovine papilloma virus, or the like.

While the wild-type sequences of FAF1 will generally be employed, in some situations one or more mutations or minor modifications may be introduced, such as deletions, substitutions or insertions resulting in changes in the amino acid sequence, providing silent mutations or modifying amino acid residues or amino or carboxyl terminal groups. Conservative amino acid substitutions can be introduced. These amino acid changes can be made using techniques such as PCR or site-directed mutagenesis.

There will be circumstances where gene fusions between FAF1 and another protein can be useful. The fusion proteins will be recombinantly produced. The recombinant nucleic acid sequences used to produce fusion proteins of the present invention will often be derived from natural or synthetic sequences. The FAF1 nucleic acid or fragments thereof find use in the construction of vectors encoding fusion proteins.

Fusion proteins encoded by FAF1 fused to the GAL4 DNA binding domain can be used in the yeast two hybrid system to isolate any proteins other than Fas that interact with the FAF1 protein, in particular, proteins that act downstream of FAF1. The yeast two-hybrid system is described above and in the experimental examples. This method allows the isolation of the cloned genes for the interacting proteins and eventually the identification of the interacting proteins. Knowledge of the interacting proteins in the Fas signaling pathway will allow the screening of drugs for agonists and antagonists of Fas dependent apoptosis.

The nucleic acid constructs will be useful to introduce into cells, providing an efficient and economical means to produce commercially useful quantities of the protein compositions. Transfected cells producing varying quantities of full length FAF1 will also be useful in evaluating the effect of overexpression of FAF1 on Fas function and apoptosis. Nucleic acid constructs expressing various lengths and mutant forms of FAF1 can be used to determine structure-function relationships.

The means of introduction of the expression construct into a host cell will vary depending upon the particular vector and the target host. Introduction can be achieved by any convenient means, including fusion, conjugation, transfection, transduction, electroporation, injection, or the like. See, e.g., Sambrook, et al. (1989), supra. Transient or stable transfection procedures can be used. The FAF1 nucleic acid compositions are introduced into the appropriate cellular host under conditions which favor expression of the polypeptide and isolation of the resultant expressed polypeptide. This implies using an expression vector compatible with the host cell, the vector containing the necessary elements described above for expression of the polypeptide. The transfected cells are then provided with the optimum nutrient, gas and temperature conditions for optimal protein production. These conditions will depend on the cell type.

The host cells will normally be immortalized cells, i.e., cells that can be continuously passaged in culture. For the most part, these cells will be convenient mammalian cell lines which are able to express a FAF1 protein and, where desirable, process the polypeptide so as to provide an appropriate mature polypeptide and transport the mature protein to the appropriate cell compartment. By processing is intended glycosylation, ubiquitination, disulfide bond formation, general post-translational modification, or the like.

A wide variety of both prokaryotic and eukaryotic hosts will be employed for expression of the proteins and peptides. Useful hosts include bacteria, such as *E. coli.*, yeast, filamentous fungi, insect cells such as Sf9, mammalian cells, typically immortalized, e.g., various mouse cell lines, monkey cell lines, Chinese hamster ovary cell lines, human cell lines, derivatives of them, or the like. Since FAF1 appears to be ubiquitous in expression by Northern analysis, it can be expressed in most mammalian cell type. Cells that are amenable to transfection and in vitro cell culture manipulation are preferred. In a specific embodiment, Cos and L cells are used. In a preferred embodiment, FAF1 and fragments thereof are expressed in tumor cells and cells of lymphoid, thymus or heart smooth muscle and epithelial cells of murine or human origin, depending on the FAF1 species used. In some cases, the cells will be derived from a neoplastic host cell or wild-type cells will be transformed with oncogenes, tumor causing viruses or the like. Cells carrying the FAF1 nucleic acid compositions are covered by this invention.

Uses of FAF1 Transfected Cells

Cells transformed with the nucleic acid compositions can be used to create transgenic mice. Such transgenic mice are useful e.g. to study the effect of overexpression of FAF1 on growth and development of the animal. The procedure for producing transgenic mice is known in the art and are described in detail in Hogan et al., *Manipulating the Mouse Embryo*, Cold Spring Harbor laboratory, Cold Spring Harbor, N.Y. (1986). Mice having homozygous deletion of the FAF1 gene (knockout mice) can also be generated by homologous recombination using gene targeting techniques (see, e.g., Capecchi, *Science*, 244:1288–1292 (1989). Such knockout mice are of interest to study the affect of FAF1 deficiency on development and cell differentiation.

Another aspect of the invention relates to methods of screening for agonists and antagonists of FAF1 which can affect apoptosis mediated by the Fas pathway. The agonists and antagonists are preferably small molecules defined as being in the range of MW 5–20 kD and can cross the plasma membrane or be taken up by the cell. Test molecules will include oligonucleotides, lipids, toxins, hormones, sugars, cofactors, peptides, small proteins, drugs and compounds from plant or animal sources and recombinantly produced substances. FAF1 transfected cells (FAF1 transfectants) are useful for such screening although cells naturally expressing Fas and FAF1 can also be used.

The screening method involves contacting a cell expressing both Fas and FAF1 with a test molecule, activating Fas, and analyzing the cell for any effects on apoptosis, increased apoptosis indicative that the test molecule is an agonist and decreased or loss of apoptosis indicative that the test molecule is an antagonist. Fas can be activated by providing Fas ligand to the cell culture media or solution of the cell sample, to bind the Fas receptor on the cell surface. Alternatively, Fas can be activated by crosslinking with antibodies to the extracellular domain of Fas. If Fas is expressed as a fusion protein, an antibody specific to the extracellular domain portion of the fusion protein will be used to crosslink Fas. For example, an anti-CD4 antibody can be used to crosslink a CD4/Fas fusion protein. FAF1 can be naturally or recombinantly produced in the wild type form or expressed as a fusion protein. Appropriate positive and negative control cells will be required for comparison.

In one embodiment, L cells expressing a Fas fusion protein, such as the CD4/fas-16 cells described in the Experimental Examples, are further transfected with FAF1 or mock transfected with vector as described. The mock transfected CD4/fas-16 serve as negative control for the functional assays. Transfectants expressing both Fas and FAF1 (test cells) and mock transfectants expressing Fas only (negative control cells), are contacted with a solution sample containing one or more test compounds. A sample of double transfectants will be treated under the same conditions but in the absence of the test molecule. The cells can be exposed to the test compound added to the culture media. The test compounds can initially be screened in pools comprising about 2–10 different compounds or molecule types per sample solution.

Cells treated in the absence or presence of the test Molecule will be tested for e.g. for disruption of Fas-FAF1 interaction or for any effect on apoptosis with or without stimulation of Fas. In one embodiment, the cells are crosslinked with anti-CD4 antibody (e.g., L3T4) and then assayed for any effects on FAF1 activity essentially as described in the Experimental Examples under the subsection Association of FAF1 with Fas. The cells are analyzed for morphological changes such as cell membrane blebbing and other characteristics of apoptosis. Cellular DNA can be analyzed for fragmentation by gel electrophoresis. Based on these criteria, the percentage of apoptotic cells in the test cells as compared to similar cells treated in the absence of the test molecule or the mock transfected cells can be determined. The test molecule is considered an agonist if the test cells contacted with the test molecule show increased frequency of apoptosis over the negative control. In contrast, loss of or reduction in apoptosis in the test cells is indicative that the test molecule is an antagonist.

In a specific embodiment, peptide libraries expressing peptides of about 8–15 amino acids, preferably 10–12 amino acids in length (10–12 kD), are screened for agonistic or antagonistic effects on FAF1 activity. The generation and screening of synthetic peptide combinatorial libraries is described, e.g., in Houghten et al., *Nature*, 354:84–86 (1991). Libraries of peptide ligand can also be screened using the bacteriophage surface display technology as described by Djojonegoro et al., *Biotechnology*, 12:169–172 (1994).

Isolation of FAF1 Polypeptide

The FAF1 polypeptide can be isolated from a normally expressing cell or a transfected cell by immunoprecipitation or affinity chromatography of cell lysates using FAF1-specific antibody. The antibody can be in solution or affixed on a solid substrate. It may be more efficient to isolate the protein from transfected cells that may produce larger quantities of the protein due to particular characteristics of the expression construct, such as a strong promoter. Instead of or in addition to immunological methods, the peptide will generally be isolated by techniques employing FPLC, HPLC, electrophoresis, gradient centrifugation and other methods routinely used in protein purification to provide a substantially pure product, i.e., particularly free of cellular contaminants. For protein purification methods, see, e.g., Jacoby, *Methods in Enzymology*, Vol. 104 (1984), Academic Press, New York; Scopes, *Protein Purification: Principles and Practice*, (2nd Ed.) (1987) Springer-Verlag, New York; Deutscher (ed.), *Guide to Protein Purification, Methods in Enzymology*, Vol. 182 (1990).

Uses of FAF1 Polypeptide Compositions

The FAF1 polypeptide compositions find several uses.

The polypeptide compositions of FAF1 are useful for raising antibodies, both polyclonal and monoclonal. Such antibodies are powerful tools that can be employed in various assays and diagnostic situations particularly where immunoprecipitation, immunoblotting and affinity purification procedures are necessary. Thus, one aspect of the invention is to provide antibodies that specifically bind to the FAF1 polypeptide comprising the sequence of SEQ ID NO:2, an allelic or species variation thereof, or a fragment thereof. Antibodies capable of specifically blocking the binding of FAF1 to Fas are also desirable reagents. The invention provides a rabbit antiserum produced using the entire FAF1 as immunogen. This rabbit anti-FAF1 antiserum is useful in both immunoprecipitating FAF1 and detecting FAF1 on Western blots. The invention also provides hybridoma lines that produce monoclonal antibodies to the FAF1 polypeptide.

These antibodies find use in isolating the FAF1 protein and any structurally related proteins expressing an epitope recognized by the anti-FAF1 antibody. Isolation of FAF1 and structurally related proteins can be accomplished by simply immunoprecipitating the proteins from lysates of normally expressing or transfected cells. Alternatively, affinity purification of, e.g., cell lysates can be performed using the FAF1 antibody fixed on a solid matrix such as a column of beads or a filter paper.

FAF1 antibodies are also useful to study the interaction of FAF1 with Fas in vivo, in normal and growth dysregulated or cancerous cells. The same protocol described in the experimental examples for studying the interaction of FAF1 with Fas in intact cells can be followed.

Thirdly, the FAF1 specific antibodies find use in isolating any FAF1 associating protein that co-immunoprecipitates with FAF1. FAF1 associating proteins are useful to study the downstream effectors of Fas and the regulation of Fas and FAF1 function.

In a different aspect, FAF1 specific antibodies can serve as diagnostic reagents to detect deficiencies in FAF1 such as expression levels in cells from patients suffering from certain autoimmune diseases or tumor cells from cancer patients.

Polyclonal and/or monoclonal antibodies with specificity to FAF1 can be prepared by in vitro or in vivo techniques following standard procedures as described in, e.g., Harlow, et al., *Antibodies: A Laboratory Manual* (1988), Cold Spring Harbor Press, New York. Antibodies are produced by immunizing an appropriate vertebrate host, e.g., rabbit or rodents, with the entire FAF1 protein or peptides derived thereof, or in conjunction with an adjuvant. Usually two or more immunizations will be involved, and the blood or spleen will be harvested a few days after the last injection.

For immunization, preferably peptides corresponding to regions of the protein comprising hydrophilic residues or residues exposed to the aqueous phase are selected. Immunogens comprising peptides corresponding to the region in FAF1 that interacts with Fas are desirable. Synthetic peptide fragments may be prepared in a peptide synthesizer and coupled to a carrier molecule (e.g., keyhole limpet hemocyanin) and the conjugate injected into rabbits at selected times over several months.

For production of polyclonal antibodies, an appropriate host animal is selected, typically a rabbit or a mouse. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species will sometimes be substituted for a mouse or rabbit, including goats, sheep, cows, guinea pigs, and rats.

The rabbit or mouse sera is tested for immunoreactivity to the FAF1 protein or peptide immunogen by an immunoassay, typically with preimmune sera as one of the negative controls. The immunoassay can be a radioimmunoassay, an enzyme-linked assay (ELISA), a fluorescent assay, or any of many other choices, most of which are functionally equivalent but may exhibit advantages under specific conditions.

The polyclonal antibodies can be provided commercially in the form of antisera or in purified form. From the polyclonal antisera, the immunoglobulins may be precipitated, isolated and purified, such as by affinity purification. Preferably, the purified form is substantially free of non-specific antibodies and cellular contaminants.

Monoclonal antibodies with affinities of $10^8$ $M^{-1}$ preferably $10^9$ to $10^{10}$, or stronger will typically be made by standard procedures as described, e.g., in Harlow et al., *Antibodies: A Laboratory Manual*, CSH Laboratory (1988); or Goding, *Monoclonal Antibodies: Principles and Practice* (2d ed) (1986), Academic Press, New York. Normally, mice are used to produce monoclonal antibodies although rats, guinea pigs and other animals can also be used. After the appropriate period of time from the immunization schedule, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al., "Generation of a Large Combinatorial Library of the Immunoglobulin Repertoire in Phase Lambda," *Science*, 246:1275–1281 (1989).

The polypeptides and antibodies of the present invention may be used with or without modification. Frequently, the polypeptides and antibodies will be labeled by conjugating, either covalently or non-covalently, a substance which provides for a detectable signal.

A wide variety of labels and conjugation techniques are-known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

The FAF1 antibodies of the invention can also be provided in a kit, with or without a FAF1 polypeptide, for use in any of the various applications described above. The contents of the kit will vary depending on the intended application of the antibody and may include other reagents and instructions for the use of the antibody preparation and the reagents. At least one aliquot of the antibody will be provided. Different FAF1 antibodies with specificities for different regions of the protein can be provided. Different antibodies may be desirable for verification of an assay result. The aliquots can be contained in any suitable container such as a vial or a tube. The polyclonal antibody can be in the form of antisera or affinity purified. Monoclonal antibodies can be provided in the form of ascites, culture media or a buffer such as phosphate buffered saline solution. The antibody preparation can be provided in solution or in lyophilized form, and may even be immobilized on a substrate such as a column matrix. The antibody preparation may also contain in it preservatives such as sodium azide or protease inhibitors such as EDTA. A carrier protein such as BSA or ovalbumin, usually between 0.5–5%, may be included for stability. The solution form of the antibody, especially the purified form, may contain up to 50% glycerol if the kit is to be stored frozen at −20° C. to −70° C. If the antibody is provided in lyophilized form, the kit can include a reconstitution buffer to reconstitute the antibody.

If the antibody is to be used in Western blot analysis, reagents for use in the Western blot procedure can be included in the kit. A secondary, labeled antibody capable of binding to the FAF1 antibody allowing detection of the bound FAF1 antibody, can be included. The labeled antibody may be conjugated to an enzyme such as alkaline phosphatase or horse radish peroxidase.

A FAF1 polypeptide included in the antibody kit will be useful as a control such as for molecular weight indicator on the blot and antibody detection. FAF1 polypeptides by themselves can also be provided in separate kits or vials for the various uses described. It is possible that FAF1 may have lipase activity. If FAF1 is enzymatically active, it may be provided in a kit for use as an enzyme.

The invention also provides methods of isolating a FAF1 associating protein. As used herein, the terms "FAF1 associating protein" and "FAF1 interacting protein" have the same meaning. A first method comprises contacting a cell lysate suspected of containing a FAF1 associating protein with a FAF1 polypeptide and isolating any protein bound to said FAF1 polypeptide as a FAF1 associating protein. The FAF1 polypeptide can be isolated from cells that normally produce FAF1 at high levels or from FAF1 transfected cells that overexpress FAF1. For this purpose, FAF1 encompasses full length FAF1, fragments of FAF1 or FAF1 fusion proteins. A convenient source of FAF1 are the cells transfected with HA epitope-tagged FAF1 of the present invention.

In one embodiment of the first method, a FAF1 polypeptide is immobilized on a solid matrix. The solid matrix can comprise various materials such as is commonly used in column chromatography, including sepharose, sephadex, agarose, polystyrene and latex beads. The solid matrix can also be filter paper or membrane, such as nitrocellulose and polyvinylidene fluoride (PVDF) membrane. The FAF1 polypeptide can be coupled to the solid matrix directly or indirectly. Direct methods include covalent coupling to sepharose beads using cyanogen bromide. Indirect coupling can take advantage of an FAF1 antibody or some other moiety suitable for linking the two components such as biotin-avidin binding pairs. FAF1 or FAF1 fusion proteins may be more conveniently immobilized if the fusion protein can bind a ligand provided on the matrix.

Lysates are prepared from FAF1 expressing cells. Cell lysates will be contacted with the immobilized FAF1 polypeptide such as by running the lysates over a FAF1 affinity column to allow any FAF1 interacting protein to bind the immobilized FAF1 polypeptide under optimum conditions. Preferably the binding reaction is carried out between 4° C. and normal physiological temperature. Buffer conditions can be modified to favor capture of this binding. For example, the Ph and salt conditions can be varied. The matrix is then washed with buffer to remove any unbound or nonspecifically bound cellular components. Any protein that has bound to the FAF1 polypeptide will be isolated by elution off the solid matrix such as by using a salt gradient or using soluble FAF1 polypeptide and fragments thereof to compete for binding.

In a second method, FAF1 expressing cells, preferably transfectants that overexpress FAF1, are biosynthetically labeled in order to label the proteins. For this method, the cells to be transfected with FAF1 or FAF1 fragments are preferably cells that naturally express FAF1 so as to favor the likelihood of the cells also expressing a FAF1 associating protein. It is likely that the Fas pathway has to first be activated to induce a FAF1 interacting protein to associate with FAF1. Therefore, a sample of cells treated to activate Fas will be tested in parallel. As mentioned earlier, Fas can be activated by binding to Fas ligand (FasL) or by anti-Fas antibody cross-linking. If CD4/fas fusion protein expressing transfectants (such as CD4/fas-16 described below) are used, Fas can be cross-linked using anti-CD4 antibodies (e.g., L3T4). The cells are lysed under different detergent conditions and FAF1 is immunoprecipitated from the labeled cell lysate using anti-FAF1 antibody or antiserum. Labeled proteins that co-immunoprecipitate with FAF1 are identified by SDS-PAGE followed by autoradiography.

A third method for isolating FAF1 associating proteins involves screening a phage or bacterial peptide library for peptides capable of binding to FAF1 and isolating any bound peptide by affinity purification. Fodor et al. in U.S. Pat. No. 5,143,854 describe methods of preparing arrays of peptides on a solid matrix, screening of the peptides and automated detection of peptides bound to ligand. The FAF1 polypeptide can be provided in substantially pure form, immobilized directly or indirectly onto a solid matrix. FAF1 can also be provided as an immunocomplex containing FAF1 bound to an antibody that specifically recognizes a tag on FAF1. A HA epitope tag and an anti-HA epitope antibody combination is a suitable example. The tag antibody can be covalently bound to a solid matrix such as protein A-sepharose beads or directly conjugated to plain sepharose beads. Phage or bacterial peptide libraries are exposed to the FAF1 protein to allow one or more peptides to bind to the protein. Peptides which bind FAF1 are considered associated proteins and can be isolated by affinity purification.

Yet another approach to identifying FAF1 associating proteins is by using the yeast two-hybrid system and FAF1 fusion proteins as described earlier. Peptide expression libraries such as by phage display methodology, can be screened for ligand binding to the FAF1 polypeptide or fragments thereof or fusion proteins thereof.

FAF1 or FAF1 fusion proteins also find use to detect FAF1 interacting proteins by Western blotting, using the FAF1 protein in solution to bind cell lysate proteins immobilized on the blot and detecting the bound FAF1. In this circumstance, FAF1 protein can be labeled directly or indirectly. Indirect labeling will include, e.g., a labeled antibody binding to FAF1.

FAF1 can be fused, e.g., with glutathione-S-transferase (GST), to produce GST-FAF1 fusion proteins. Expression vectors carrying GST sequence and specifically constructed to facilitate recombinantly producing GST fusion proteins are commercially available from, e.g., Pharmacia. The fusion proteins may also comprise FAF1 or fragments thereof fused to the product or polypeptide encoded by a second gene. A product encoded by only a portion or a fragment of the second gene instead of the entire gene, may be sufficient. For example, FAF1 or a fragment thereof may be fused to a second gene such as the *E. coli* lacZ gene that will allow detection of expression. Other convenient fusion proteins will comprise FAF1 or fragments thereof linked to a tag.

In constructing fusion proteins, it will be understood that the amino or carboxy terminus of the FAF1 protein, or wherever the fusion junction is, may be modified to facilitate cloning or for other reasons, e.g., to allow cleavage of the fusion protein and release of the separate portions.

The tag can be a label or some means that allows identification of the fusion protein. The tag is introduced into a site in the polypeptide that will not interfere with the folding and the function of the protein, generally at the N- or the C-terminus. The tag can be an epitope tag recognizable by an antibody, a member of a binding pair, an enzyme or any other suitable entity. The tag can be a cleavable sequence such as the phosphatidylinositol-glycan (PIG) signal sequence present in proteins such as alkaline phosphatase, DAF and acetylcholinesterase. The PIG sequence is cleavable by the enzyme phosphatidylinositol phospholipase C (PI-PLC) (Ferguson, *Ann. Rev. Biochem.*, 57:285–320 (1988)). The influenza virus hemagglutinin (HA) and the myc epitopes are particularly useful tags. Examples of binding pairs are ligand-receptor, antigen-antibody and small molecules like avidin-biotin. Enzyme tags include horse radish peroxidase, alkaline phosphatase and β-galactosidase which can act on a substrate to produce a color signal. For example, the protein can be fused to an epitope tag recognizable by an available antibody. The antibody to the tag is useful, e.g., to immobilize the FAF1 protein on an affinity column or to detect the protein such as when the fusion protein is used in Western blotting.

The invention also provides a method to block or modulate FAF1's ability to potentiate Fas-mediated apoptosis in vitro and in vivo. The method involves using peptides corresponding to the Fas-interacting domain of FAF1 to compete with endogenous wild-type FAF1 for associating with Fas. The Fas-interacting domain or region of FAF1 is determined as described above. By competing for binding to Fas, the Fas-interacting domain peptide will block or reduce the ability of wild-type FAF1 to interact with downstream effector molecules. This, in turn, will affect the cellular signalling events downstream of Fas.

The method of blocking Fas activity comprises providing a Fas-interacting domain peptide of FAF1 in a cell expressing Fas and FAF1 wherein the Fas-interacting peptide will bind to the Fas protein to block Fas activity. The Fas-interacting domain peptide itself can be directly introduced into the cell under study where arrest or modulation of Fas function is desired. Methods of introducing the Fas-interacting domain peptide into the cell include microinjection of the isolated peptide (expressed in other cells) or the use of appropriate drug delivery vehicles such as liposomes to deliver the polypeptide.

Alternatively, the Fas-interacting domain peptide can be provided by introducing an expression construct encoding the Fas-interacting domain peptide into the desired cell wherein the Fas-interacting domain peptide will be expressed in an amount effective to interfere with Fas activity. Expression constructs can be targeted to a particular cells by using nucleic acid delivery vehicles that contain targeting moieties on the surface of the vehicle. Examples of such vehicles include liposomes or recombinant viruses expressing receptors for cell surface markers. In some circumstances, complete blockage of Fas activity may require high level expression i.e. overexpression of the Fas-interacting domain peptide for effective competition. In that circumstance, the expression construct can be designed to contain the necessary elements such as strong promoters, inducible promoters and enhancers to achieve high level expression of the Fas-interacting domain peptide. The Fas-interacting domain peptide expressed intracellularly will be contacted with and bind to the Fas protein.

Therapeutic Uses

An important embodiment of the invention is the treatment of diseases in which apoptosis is dysregulated. The treatments will have the potential to change the natural progression of some of these diseases. Such therapeutic treatments will involve either the induction or the inhibition of apoptosis through FAF1, depending on the particular disease condition. The invention provides therapeutic formulations and methods of using these formulations to treat diseases.

The following lists examples of diseases where cells fail to undergo apoptotic cell death. In such diseases, it would be desirable to induce selective apoptosis in the affected cells so as to remove autoreactive cells, cancerous cells or viral infected cells that cause the disease. The diseases include: 1) Cancers, e.g., follicular lymphomas, carcinomas with p53 mutations, hormone-dependent tumors such as breast cancer, prostate cancer and ovarian cancer; 2) Autoimmune disorders, e.g., include systemic lupus erythematosus (SLE) and immune-mediated glomerulonephritis; and 3) Viral infections such as caused by herpesviruses, poxviruses and adenoviruses. Such viral infections include fulminant hepatitis.

Several approaches for inducing or enhancing apoptosis are contemplated in the present invention. One approach is to bypass Fas by providing a constitutively active FAF1 that is functional in activating downstream events leading to apoptosis, independent of Fas activation by Fas ligand binding or Fas antibody cross-linking. The generation of a constitutively active FAF1 has been described above. The lpr$^{cg}$/lpr$^{cg}$ mouse and human patients that manifest the lpr phenotype can be used here as a model. Due to a mutation in Fas, the lprcg/lprcg mice develop lymphadenopathy and autoimmune disease and produce large quantities of autoantibodies. The autoreactive B cells or certain subsets of these B cells can be targeted for apoptotic cell death by introducing a constitutively active FAF1 into these cells.

One method of providing a constitutively active FAF1 to a target cell is by gene therapy. A recombinant DNA molecule (expression vector) encoding the constitutively active FAF1 is introduced into the cell whereby the active FAF1 is expressed. The expression vector will be selectively delivered to the target cells only so as not to affect killing of all cells. Targeted delivery of DNA can be done for example by using delivery vehicles such as liposomes or viral vectors which have targeting moieties on the surface. Liposome delivery vehicles with targeting moieties are described in more detail below. Basically, the delivery vehicle will contain on its surface, a targeting moiety that recognizes and binds a specific cell surface marker. In the example of targeting delivery of the DNA to a specific clonal population of B lymphocytes, the membrane immunoglobulin expressed on the B lymphocyte serves as one convenient cell surface marker. The targeting moiety can be an anti-idiotype antibody (the entire antibody or only the Fab region) that recognizes the specific surface immunoglobulin expressed by the B lymphocyte population. In this manner, the recombinant DNA expression vector incorporated into the liposome can be specifically delivered to the target cell population.

Recombinant viral vehicles can similarly be designed to express a targeting moiety on the viral capsid or envelope. It should be noted that the targeting moiety can be a member of any binding pair combination and is not limited to that just antibody-antigen pairs. The viral delivery vehicle will contain in its viral genome, the sequence encoding the constitutively active FAF1. The recombinant viral DNA can be designed to achieve targeted integration of the FAF1 sequence into the genome of the target mammalian cell.

Other methods of introducing FAF1-encoding DNA into affected B cells include local injection of naked DNA into lymph nodes or spleen.

The next set of diseases are associated with accelerated rates of physiological cell death and characterized by cell loss. In these diseases, it would be desirable to provide therapeutic intervention to block or modulate the exacerbated Fas-mediated apoptosis. The disease conditions include ischemic injury such as caused by myocardial infarction (smooth muscle and epithelial cell death), stroke induced neuron death and reperfusion injury; AIDS; and liver disease caused by viral infection, such as fulminant hepatitis.

Methods to block the activation of FAF1 through Fas include the use of (i) antagonists that are small molecules, (ii) peptide inhibitors and (iii) antisense inhibition. Again, liposomes can be used to target delivery of the small molecular and peptide inhibitors as well as antisense nucleic acids to specific cell populations.

Small molecule antagonists and peptide inhibitors have been discussed above. Peptide inhibitors include peptides corresponding to regions of FAF1 that interact with Fas or with effector molecules of FAF1 or that exhibit an enzymatic activity. Peptide inhibitors are intended to inhibit interactions between Fas and FAF1, Fas and effector molecule or Fas and substrate.

For a review of antisense therapy, see, e.g., Uhlmann et al., *Chem. Reviews*, 90:543–584 (1990). The antisense oligonucleotides will be complementary to and hybridize specifically to the FAF1 mRNA, thus inhibiting translation of the mRNA and in addition, resulting in the RNAse H cleavage of the bound mRNA. The antisense oligonucleotides can be DNA or RNA although DNA is preferred because of greater stability. They can be chemically modified so as to improve stability in the body. The antisense oligonucleotide will be at least 15 nucleotides but generally 17 nucleotides (MW about 5,000) or longer. RNA oligonucleotides can be provided in the form of ribozymes designed to cleave the mRNAs to which they bind. The ribozymes will comprise RNA or mixed RNA-DNA oligonucleotide.

The disease conditions described such as exacerbated cell death due to myocardial infarction or stroke can be treated by administering to the patient, a therapeutic formulation comprising an inhibitor of FAF1 activity in an amount effective to block the FAF1 activity in affected cells in the patient. The inhibitor of FAF1 activity can be a Fas-interacting domain peptide. The patient can be administered a therapeutically effective amount of a pharmaceutical composition comprising a Fas-interacting domain peptide, and a pharmaceutically acceptable carrier. The Fas-interacting domain peptide will be specifically targeted to the affected cells, such as cardiac smooth muscle cells and epithelial cells in myocardial infarction, hepatocytes in fulminant hepatitis, and T cells and macrophages in AIDS. Another pharmaceutical composition for use in the treatment method will comprise an expression vector suitable for introduction into and expression of a therapeutically effective amount of a Fas-interacting domain peptide in these aforementioned cells.

Drug delivery vehicles such as liposomes can be used to deliver and provide sustained release of the formulations in the body. The liposomes can have targeting moieties exposed on the surface such as antibodies, ligands or receptors to specific cell surface molecules. For example, it may be desirable to limit the delivery of the formulation to only tumor cells. Such cells can be targeted to receive the therapeutic formulation by incorporating into the liposome carrier, a targeting moiety that recognizes and binds a specific tumor surface marker. Liposome drug delivery is known in the art (see, e.g., *Biochimica et Biophysica Acta*, 113:201–227 (1992)).

The quantities of reagents determined to be an effective amount for treatment will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), *Goodman and Gilman's: The Pharmacological Bases of Therapeutics*, 8th Ed. (1990), Pergamon Press; and *Remington's Pharmaceutical Sciences*, 17th Ed. (1990), Mack Publishing Co., Easton, Pa. Methods for administration are discussed therein, e.g., for oral, intravenous, intraperitoneal, or intramuscular administration, transdermal diffusion, and others.

If the pharmaceutical composition is formulated for oral delivery and contains a peptide or peptide-like compound as the active agent, then the formulation must include a means for protecting the agent from the proteolytic enzymes of the digestive system. Typically, the agent is encased in a liposome structure or chemically derivatized so that the enzymes are prevented from cleaving the amide bonds of the peptide, resulting in the agent's degradation.

The pharmaceutical compositions will be administered by intravenous, parenteral, intraperitoneal, intramuscular, oral, or local administration, such as by aerosol or transdermally, for therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions will often be administered intravenously. Thus, this invention provides compositions for intravenous administration which comprise a solution of the polypeptide dissolved or suspended in an acceptable carrier, preferably an aqueous carrier. Slow release formulations, or slow release delivery vehicles will often be utilized for continuous administration. "Pharmaceutically acceptable carriers" will include water, saline, buffers, and other compounds described, e.g., in the Merck Index, Merck & Co., Rahway, N.J. These compositions will sometimes be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, preferably about 20% (see, Remington's, supra).

The compositions containing the compounds can be administered for prophylactic and/or therapeutic treatments. In therapeutic applications, compositions are administered to a patient already suffering from a disease, as described above, in an amount sufficient to cure or at least alleviate the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

The following examples are offered by way of illustration and are not meant to be construed as a limitation on the scope of the invention.

EXPERIMENTAL EXAMPLES
Materials and Methods

Antibodies—GK1.5, used as a primary crosslinking antibody, is a monoclonal antibody specific to murine CD4 (L3T4) (Caltag). PE-L3T4 (Caltag) is GK1.5 conjugated with PE and was used for surface staining of CD4/fas expression by Fluorescence Activated Cytometry Scanning (FACS) analysis (FACS IV, Becton-Dickinson). A rabbit Anti-Rat IgG was used as secondary crosslinking antibody (Zymed). 12CA5 is a monoclonal antibody specific for the hemaagglutinin (HA) epitope of the influenza virus (Wilson et al., Cell, 37:767–778 (1984)). A rabbit serum specific for murine CD4 (a gift from Dr. D. Littman) was used for detection of CD4/fas by Western blot.

DNA Constructs—A chimeric molecule of CD4 and fas was subcloned into vector PSM described in Brodsky et al., J. Immunol., 144:3078–3086 (1990), which has an SV40 replication origin and an SV40 early promoter. PSMCD4/fas contains the chimera with a wild type cytoplasmic domain of Fas. PSMCD4/fas786A has a T to A point mutation at base pair 786 in the cytoplasmic domain of Fas. Fusion molecules of the λ repressor dimerization domain and Fas cytoplasmic domain were inserted in frame with GAL4 DNA-binding domain and HA epitope in the vector PAS-CHY (Durfee et al., Genes Dev., 7:555–569 (1993)). FAF1 tagged with an HA epitope at the N-terminus was subcloned into the PCGN vector (with a CMV promoter) to make PCGN8.1.

Cells, Transfections and Immunoprecipitation—For co-immunoprecipitation experiments, Cos cells were transiently transfected with PCGN8.1 alone or PCGN8.1 plus PSMCD4/fas or PCGN8.1 plus PSMCD4/fas786A by DEAE Dextran method (Gorman, DNA Cloning, A Practical Approach, IRL Press, Oxford, Vol. II, pp. 143–190 (1985)). Transfectants were lysed by lysis buffer (20 mM Tris, PH7.5, 137 mM NaCl, 1% triton x 100) two days later. The expression level of FAF1 was quantitated by Western blot analysis with 12CA5 antibody. Cell lysates were used for immunoprecipitation of CD4 by GK1.5. Immune-complexes were analyzed by 8% SDS-PAGE and transferred to nitrocellulose paper. The paper was then incubated with 12CA5 antibody and developed by an alkaline phosphatase method (Boehringer Mannheim). To quantitate the amount of CD4/fas or CD4/fas786A immunoprecipitated, the blot was stripped off, re-probed with anti-CD4 serum and then developed by Enhanced Chemiluminescence (ECL) method (Amersham).

L cells were transfected with PSMCD4/fas or PSMCD4/fas786A plus a TK promoter driven neo gene expression vector (Stratagene) by calcium precipitation. The cells were then selected in medium with G418 (400 g/ml) for 10 days (Itoh et al., Cell, 66:233–243 (1991)). Individual clones were analyzed for CD4 surface expression by FACS as follows. Single clones ($1 \times 10^6$ cells) of untransfected L cells (L cells), L cells transfected with PSM vector alone (PSM-1), L cells transfected with PSMCD4/fas (CD4/fas-16) or with PSMCD4/fas786A (CD4/fas786A-23) were incubated separately with 1 μl of fluorescence (PE) conjugated anti-CD4 antibody (PE-L3T4, Caltag) in 100 μl PBS (3% FCS) at 4° C. for 30 minutes, washed twice with PBS (3% FCS), and analyzed by FACS (FACS IV, Becton-Dickinson). Multiple clones expressing either the wild type or mutant chimera were generated.

For FAF1 functional studies, PCGN8.1 or PCGN vector plus PSV-βGAL (5:1 ratio) was transiently transfected into both CD4/fas and CD4/fas786A expressing cells by either DEAE Dextran or Lipofectmin (BRL). Transfected cells were identified by their expression of β galactosidase (stained blue cells with X gal) (Harlow et al., Antibodies, A Laboratory Manual, Cold Spring Harbor Laboratory, p. 401 (1988)).

Antibody crosslinking and assays for apoptosis—CD4/fas or CD4/fas786A expressing cells were incubated with appropriate amounts of GK1.5 at 4° C. for 20–30 minutes and rinsed with 37° C. pre-warmed DME medium (0% serum). Antinomycin D (final concentration of 0.5 μg/ml) were added to the cells. The cells were then incubated at 37° C. for different times.

To detect DNA fragmentation, DNA was extracted from cells two hours after crosslinking by lysing the cells with 1%

SDS. The cell lysate was digested with proteinase K at 55° C. overnight and DNA precipitated with isoamyl alcohol. The extracted DNA was analyzed with molecular weight markers by electrophoresis in 2% agarose gel and staining with ethidium bromide.

For FAF1 functional assays, the cells were crosslinked at 48 to 72 hours after transfection. Then the cells were visualized under the microscope and photographs were taken at different times to detect changes in cellular morphology. To quantitate the percentage of apoptic cell death at a given time, the crosslinked cells were fixed, stained with Xgal and counted for the number of apoptotic cells (membrane blebbing) in 100 blue cells.

Fas-Mediated Apoptosis

In order to understand the mechanism of signal transduction in Fas-mediated apoptosis, it was first determined whether the cytoplasmic domain is sufficient to initiate an apoptosis signal. A chimeric cDNA (CD4/fas) containing the cytoplasmic domain of murine Fas linked to the extracellular and transmembrane domains of murine CD4 (CD4/fas) was made. As control, the point mutation of Fas in lpr$^{cg}$ mice (T786A) was also made as an analogous chimeric molecule (CD4/fas786A). The chimeras were stably transfected into L cells and clones expressing equivalent levels of wild type (CD4/fas) or mutant (CD4/fas786A) chimeric molecules were chosen for analysis (FIG. 1A). L cells expressing CD4/fas (CD4/fas-16 underwent apoptotic cell death when crosslinked by monoclonal antibody against CD4 (L3T4, Caltag)) in the presence of actinomycin D (Itoh et al., *DNA Cloning, a Practical Approach*, IRL Press, Oxford. Vol. II, pp. 143–190 (1991). DNA fragmentation, characteristic of apoptosis, was observed two hours after the antibody crosslinking (FIG. 1B). Cells were shrunk and detached from the bottom of the culture dish at 10 hours (FIG. 1C). However, L cells expressing the mutant chimera (CD4/fas786A-23), under the same treatment, did not undergo apoptotic cell death. Multiple clones of each type were analyzed and gave the same results. It was concluded that the cytoplasmic domain of Fas can initiate an apoptotic signal.

The results also showed that dimerization of the Fas cytoplasmic domain is sufficient to generate an apoptotic signal. The antibody L3T4 (GK1.5), used here to induce apoptosis through the Fas cytoplasmic domain, is a bivalent Rat IgG-2b. As shown in FIG. 1B, there was no significant change upon the addition of a secondary anti-Rat IgG antibody, again indicating that dimerization was sufficient for Fas activation.

Screening for Fas-Interacting Protein

An improved version of the yeast two-hybrid system (Durfee et al., *Genes Dev.*, 7:555–569 (1993) originally devised by Fields and Song, *Nature*, 340:245–246 (1989)) was used to screen for Fas interacting proteins. In order to simulate activated dimeric Fas, a fusion molecule of the λ repressor dimerization domain and the Fas cytoplasmic domain was constructed. The fusion molecule was then linked to the DNA binding domain of GAL4 for two-hybrid screening. As a control, a similar construct was made with the T786A mutation (lpr$^{cg}$ mutation) in the Fas cytoplasmic domain.

The nucleotide and amino acid sequence of murine and human Fas is provided in Watanabe-Fukunaga et al., *J. Immunol.*, 148:1274–1279 (1992) and Itoh et al., *Cell*, 66:233–243 (1991), respectively. The Fas cDNA sequence of lpr$^{cg}$ mice is disclosed in Watanabe-Fukunaga et al., *Nature*, 356:314–317 (1992). The amino acid sequence of the Fas cytoplasmic domain from wild-type mouse, cg mouse and human can also be found in Watanabe-Fukunaga et al., *Nature*, supra. λ repressor dimerization domain sequence is disclosed in Amaya et al., *Development*, 118:477–487 (1993).

The plasmid CIXD containing the λ repressor dimerization domain was obtained from Marc Kirshner. Plasmid CIXD was digested with PvuII and Bal I to release a 430 bp insert containing the dimerization domain. This insert was subcloned into the blueskript plasmid pBS at the Sma I site. The insert was then excised from pBS using the convenient linker sites, BamHI and EcoRI, present in the vector. This BamHI-EcoRI fragment was blunt-ended with Klenow.

The plasmid pAS1.FasCyt contains the GAL4 DNA binding domain fused to the Fas cytoplasmic domain. The BamHI-EcoRI blunt-ended fragment containing the λ repressor dimerization domain was inserted into pAS1.FasCyt at a blunt-ended NdeI site in between the GAL4 domain and the Fas cytoplasmic domain, producing an in-frame fusion of GAL4 DNA binding domain-λ repressor dimerization domain-Fas cytoplasmic domain in the construct pAS1/RDD/CYT. This ligation creates 4 new amino acids, RSPL (SEQ ID NO:3), at the junction of GAL4 and λ dimerization domain, and 6 new amino acids, GCRNSI (SEQ ID NO:4), between the dimerization domain and the Fas cytoplasmic domain. As a control, a similar construction was made using Fas having the T786A mutation (lpr$^{cg}$ mutation) in the cytoplasmic domain.

A GAL4 transactivation domain-tagged cDNA expression library was prepared using a murine T cell line cDNA library (a gift from Dr. S. Elledge). The yeast strains and vectors used herein as well as cDNA libraries from different cell lines, linked to the GAL-4 transactivation domain, are also commercially available from, e.g., Clontech Labs Inc., Palo Alto, Calif. The yeast reporter strain is cotransformed with the λ/Fas/GAL4 DNA binding domain fusion construct and the T cell cDNA library/GAL4 transactivation domain fusions.

More than 1.1 million clones of the T cell line cDNA library were screened for their ability to interact with the Fas fusion molecule in the two-hybrid system. Four independent clones interacted specifically with the wild type Fas constructs but not the mutant Fas constructs. Two clones had 2.2 kb inserts and two other had 2 kb inserts. Sequence analysis showed that all 4 clones were derived from the same gene and fused to the activation domain of GAL4 in the same reading frame. The inserts of the shorter 2 kb clones were missing approximately 150 bp at the 5' end and 50 bp at the 3' end of the sequence of the longer clones. A murine thymus cDNA library (a gift of Dr. M. Davis) was screened with a DNA probe consisting of 0.7 kb of the most 5' end of the 2.2 kb clone isolated by the two-hybrid screening in yeast. Two independent cDNA clones of approximately 2.6 kb were obtained from the murine thymus cDNA library.

Characterization of the FAF1 Sequence

Sequence analysis indicated that these were full length cDNAs and contained an open reading frame encoding a protein of 649 amino acids (FIG. 2A). The deduced molecular weight is 74 kD and the PI was 4.6. The translation start site contains a perfect "Kozak" consensus sequence (Kozak, M., *J. Cell Biol.*, 108:229–241 (1989)). There are two regions, amino acids 280 to 310 and 490 to 590, that are highly negatively charged and have a predicated α-helical secondary structure. There are three potential myristoylation sites located at amino acid 50, 306 and 310. There are also three N-glycosylation sites at amino acid 163, 209 and 423. No significant sequence homology of these clones was found with any complete protein sequence in available sequence data banks. This novel protein was named Fas-associated factor 1 (FAF1).

Association of FAF1 with Fas in Mammalian Cells

Figure 3A:
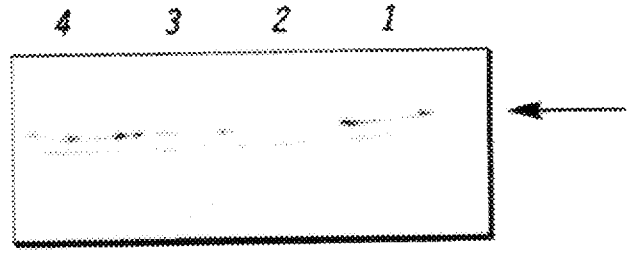
FIG. 3A shows expression of FAF1 in Cos cells detected in whole cell lysates by Western blot analysis using anti-HA epitope antibody (12CA5). The arrow indicates HA-tagged FAF1.
Figure 3B:
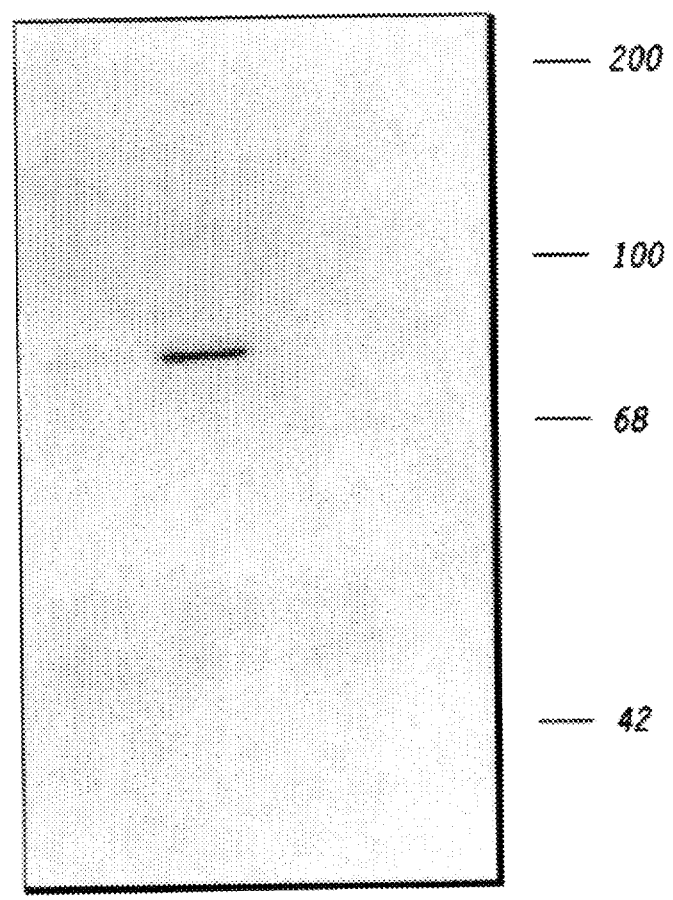
Figure 3C:
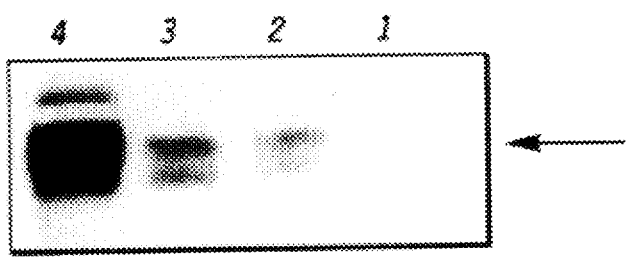

To show that the association can occur in mammalian cells, an influenza virus hemagglutinin (HA) epitope tagged FAF1 was transiently co-expressed with CD4/fas or CD4/fas786A in Cos cells. The full length 2.2 kb FAF1 cDNA was tagged at the N-terminus with a sequence encoding a 15 amino acid HA epitope and cloned into a CMV promoter-driven expression vector PCGN to produce the construct PCGN8.1. The PCGN vector is described in Klippel et al., *Mol. Cell. Biol.*, 13:5560–5566 (1993). Cos cells were transfected with PSM plus PCGN8.1 (FIG. 3A–C, lane 1), PSMCD4/fas plus PCGN (lane 2), PSMCD4/fas plus PCGN8.1 (lane 3) or PSMCD4/fas786A plus PCGN8.1 (lane 4). Two days after transfection, the cells were lysed (1% triton x100, 20 mM Tris, pH 7.5, 137 mM NaCl plus proteinase inhibitors) and 0.5% of the lysates were used to determine the FAF1 expression level by Western blot analysis with 12CA5 (FIG. 3A). Four µl of L3T4 was added to the rest of the lysates and incubated at 4° C. for one hour. 50 µl of anti-Rat IgG conjugated agarose beads (Sigma) were added and incubated for another hour. The beads were washed three times with PBS (1% NP40). The immune-complexes were electrophoresed on 8% SDS-PAGE and transferred to nitrocellulose paper. The paper was first incubated with 12CA5 and developed by an alkaline phosphatase method to detect FAF1 (FIG. 3B). The antibody was then stripped off and the paper reincubated with anti-CD4 antibody and developed by ECL to detect CD4/fas (FIG. 3C).

FAF1 was expressed equally in the Cos cells expressing either CD4/fas or CD4/fas786A (FIG. 3A). By immunoprecipitating with anti-CD4 antibody and blotting for the HA epitope, a much greater quantity of FAF1 was co-immunoprecipitated with CD4/fas than with CD4/fas786A (FIG. 3B), although more CD4/fas786A was immunoprecipitated than CD4/fas (FIG. 3C). As shown in FIG. 3B, the molecular weight of FAF1 detected on SDS-PAGE is 75–80 kD which is heavier than the predicated 74 kD. This could be accounted for by the post-translational modifications such as glycosylations of the molecule. Thus, FAF1 was able to specifically associate with the cytoplasmic domain of wild type Fas in Cos cells.

To determine the significance of the association between FAF1 and Fas, FAF1 was transiently expressed in CD4/fas-16- or CD4/fas786A-23-stably transfected L-cells. CD4/fas-16 and CD4/fas786A-23 cells were co-transfected with PSV-β Gal and PCGN8.1 or PCGN alone (1:5 ratio) by DEAE Dextran method (Gorman, *DNA Cloning, a Practical Approach*, IRL Press. Oxford. Vol. II, pp. 143–190 (1985)) or Lipofectomin (BRL). Forty-eight to seventy-two hours later, transfectants were crosslinked by different amounts of L3T4 (GK1.5) antibody in the presence of actinomycin D: 1 µg/ml (FIG. 4 C, F, I, and L) or 200 ng/ml (B, E, H and K) of L3T4 or a control rat IgG (A, D, G and J) as described in FIG. 1B. The cells were fixed and photographed one hour later.

Figure 4A:
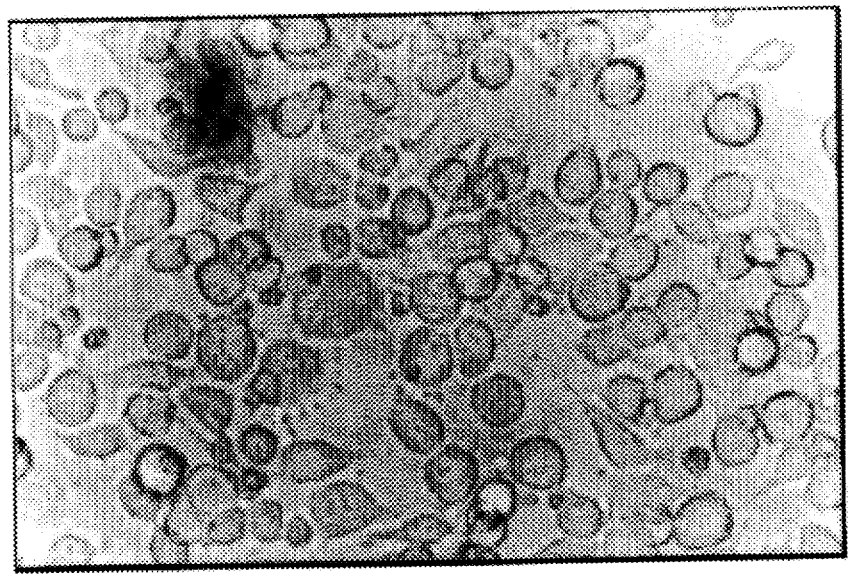
FIG. 4A–L show the morphological changes of cells expressing FAF1 after CD4/fas antibody crosslinking. A–F show CD4/fas-16 cells. G–L show CD4/fas786A-23 cells. A–C and G–I show cells transiently expressing FAF1. D–F and J–L show cells mock transfected with vector alone. CD4/fas-16 and CD4/fas786A-23 cells were co-transfected with PSV-β Gal and PCGN8.1 or PCGN alone (1:5 ratio) by DEAE Dextran method or Lipofectomin (BRL). Forty-eight to seventy-two hours later, transfectants were crosslinked by 1 µg/ml (C, F, I, and L) or 200 ng/ml (B, E, H and K) of L3T4 or a control rat IgG (A, D, G and J) as described in FIG. 1B. The cells were fixed and photographed one hour later.
Figure 4B:
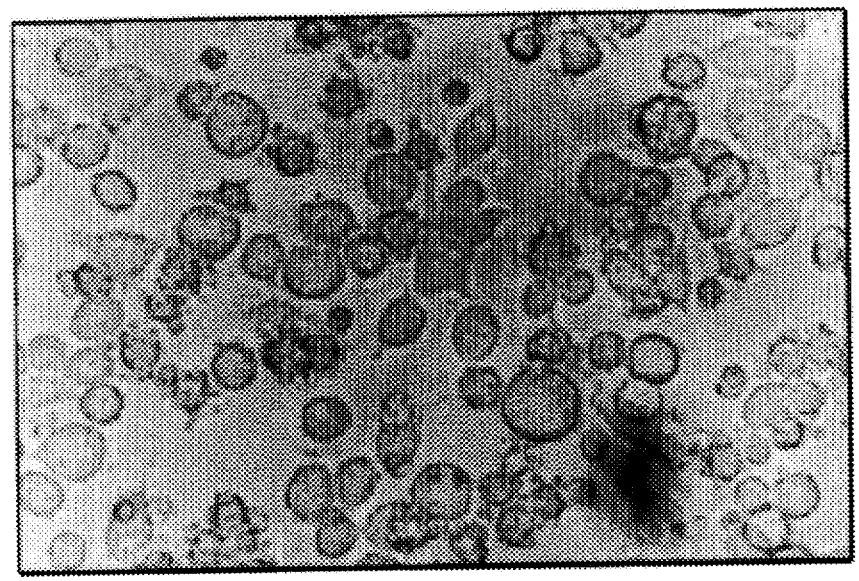
Figure 4C:
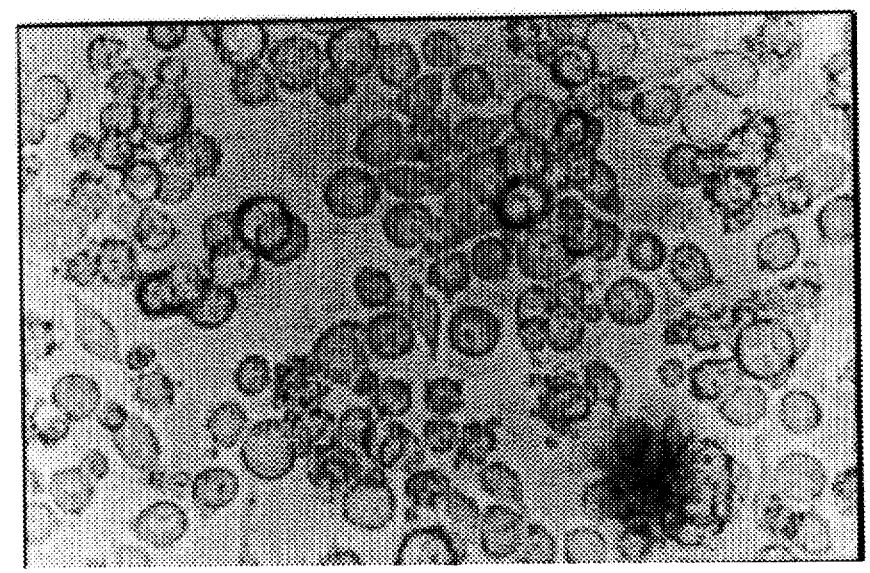
Figure 4D:
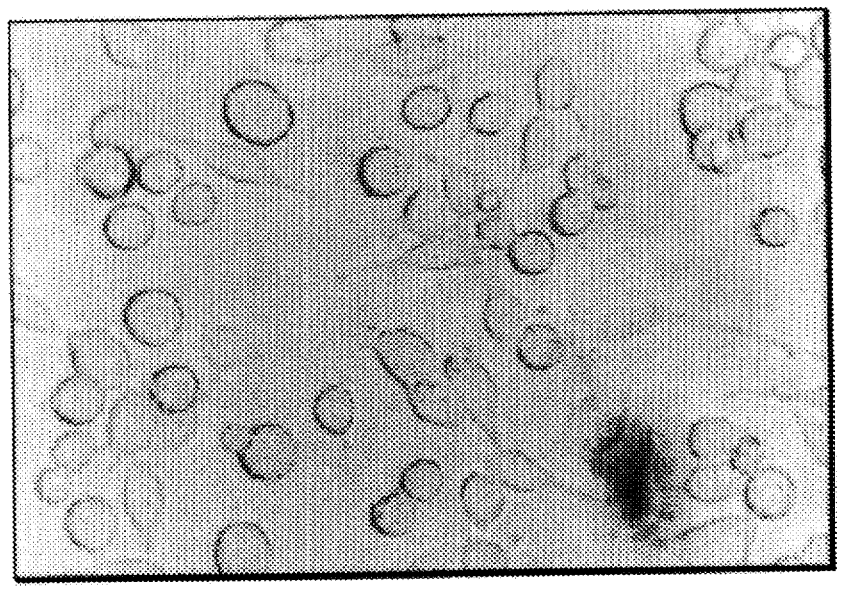
Figure 4E:
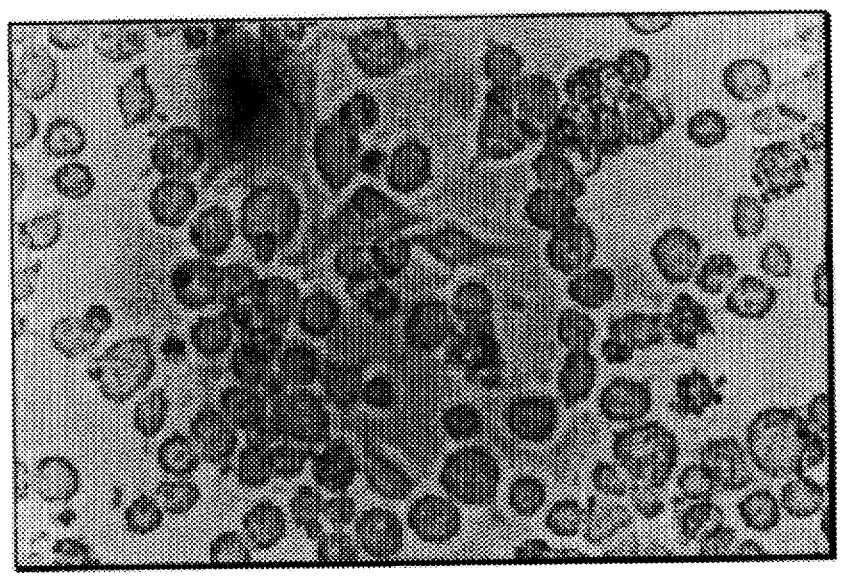
Figure 4F:
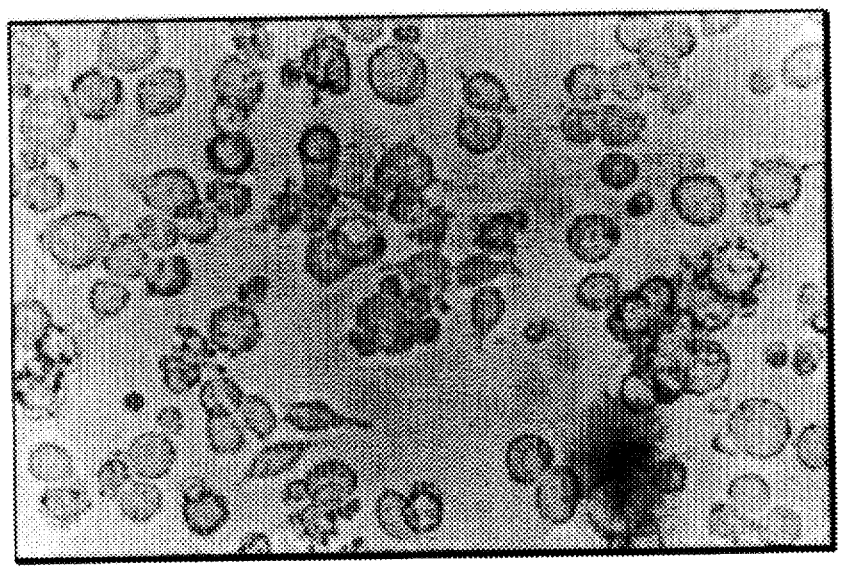
Figure 4G:
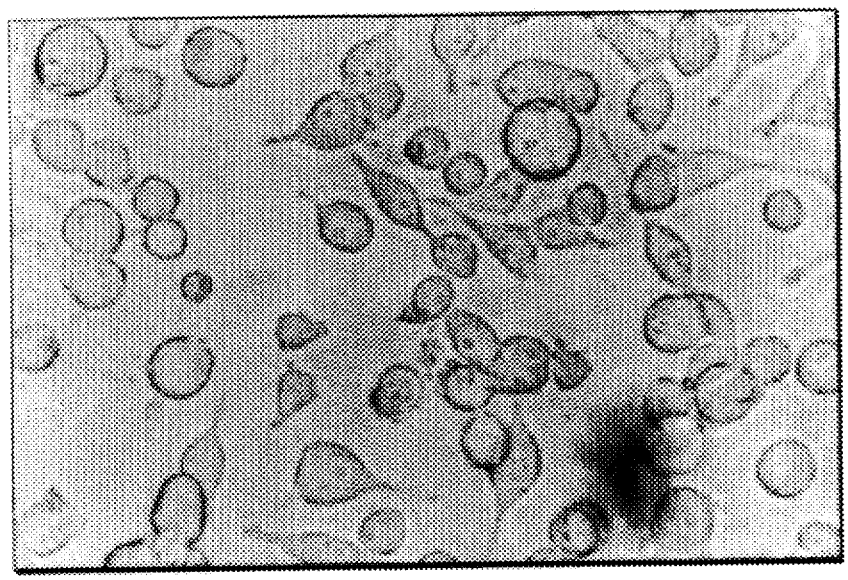
Figure 4H:
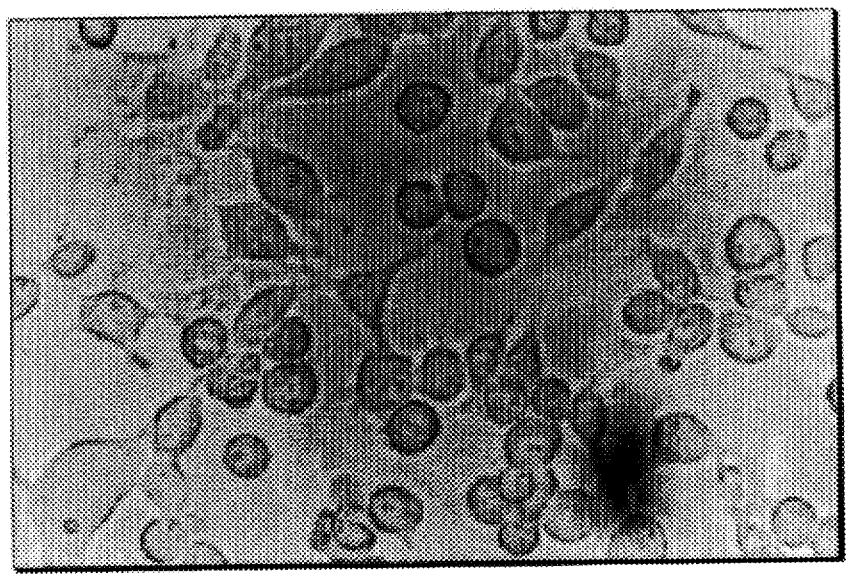
Figure 4I:
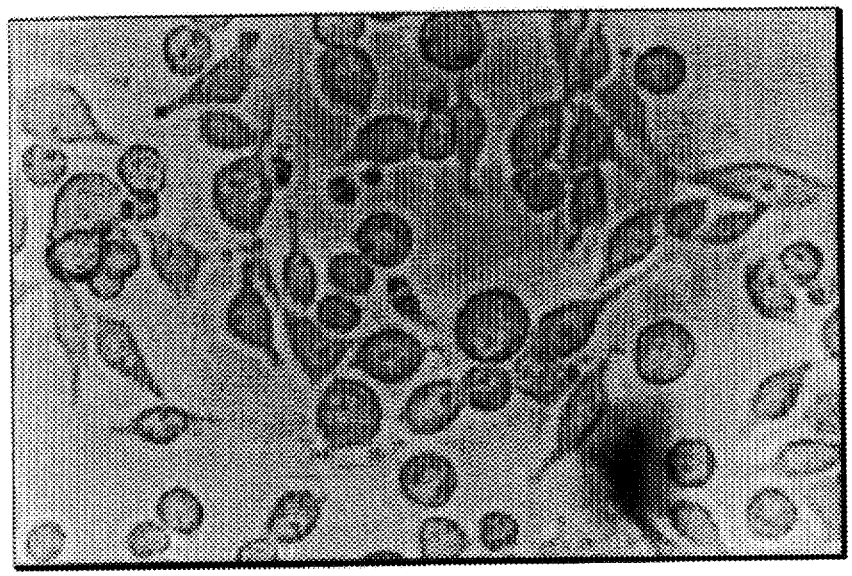
Figure 4J:
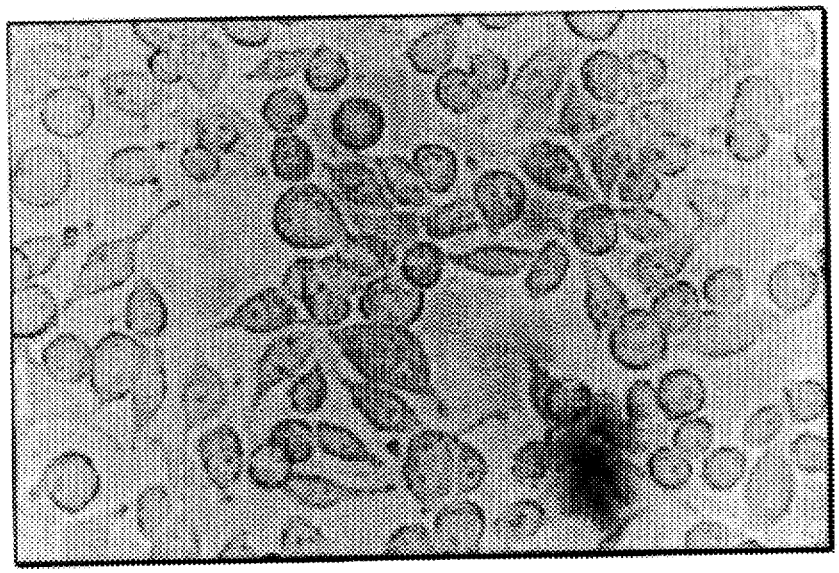
Figure 4K:
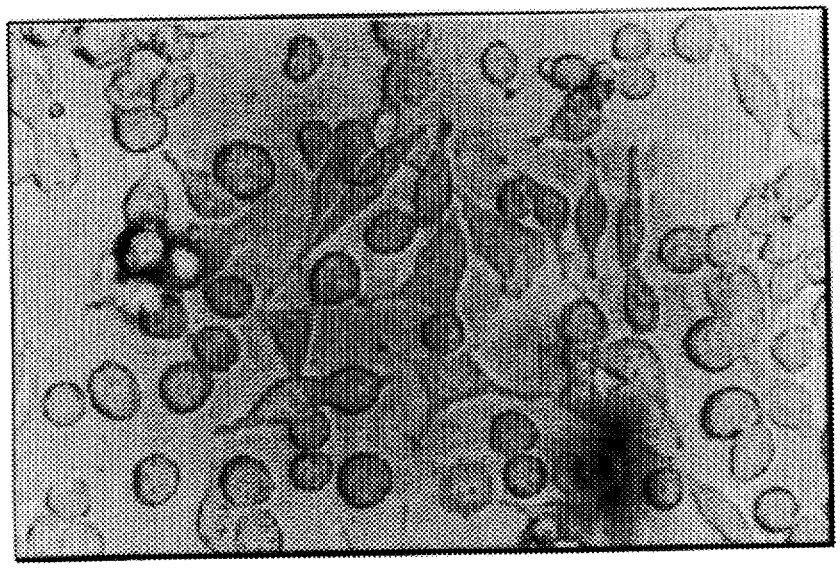
Figure 4L:
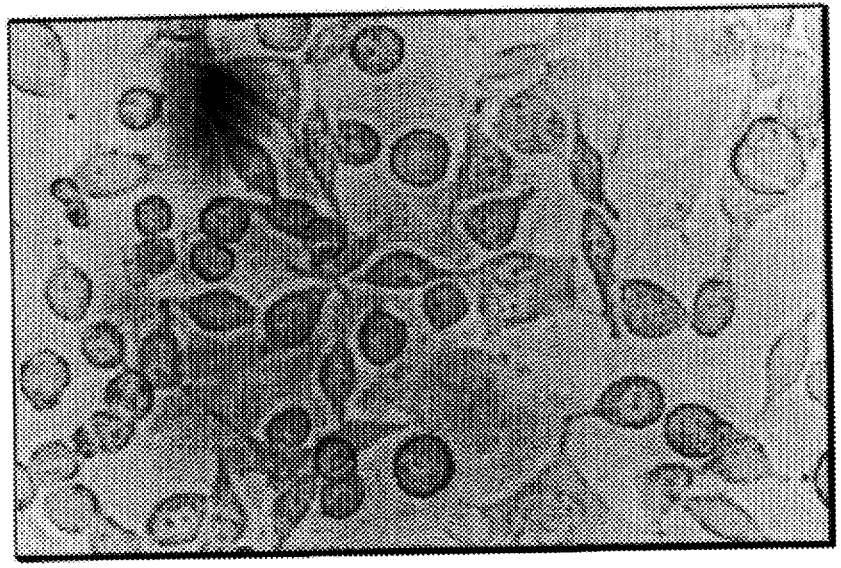
Figure 5:
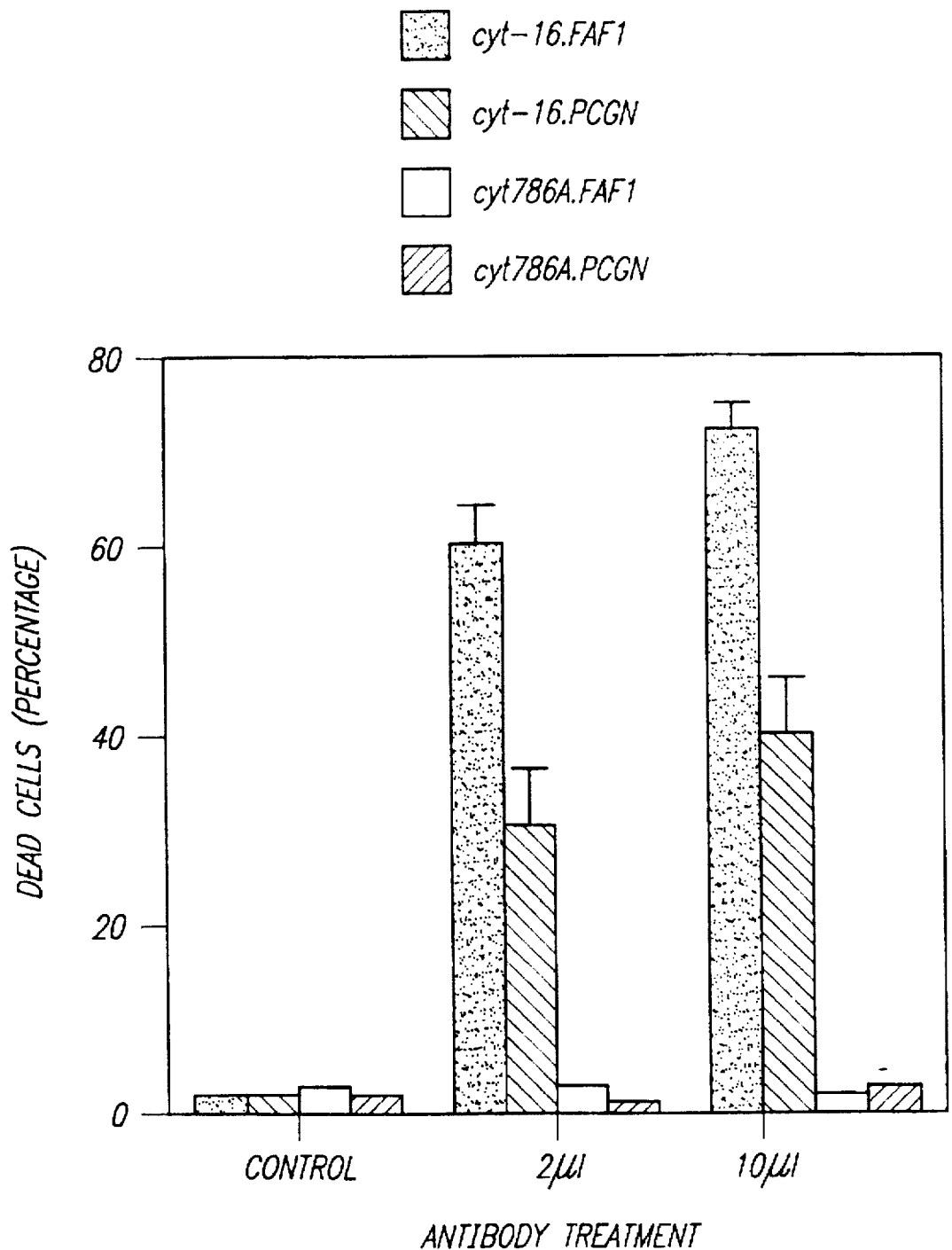
FIG. 5 shows the percentage of cells undergoing apoptosis 1 hour after L3T4 treatment. The fixed cells, from the experiment described in FIG. 4, were assayed for β-galactosidase expression and blue cells were counted by light microscopy. The percentage of apoptotic cells is the number of cells with cell membrane blebbing among one hundred blue cells counted. The bars indicate means and standard deviations for four independent experiments.

In CD4/fas-16 cells, transient expression of FAF1 resulted in more rapid and extensive apoptosis than in mock transfected cells (FIG. 4A). One hour after addition of 200 ng/ml of L3T4 crosslinking antibody, approximately 60% of CD4/Fas-16 cells expressing FAF1 had undergone apoptotic cell death compared with 30% in the cells without FAF1 overexpression (FIG. 5). Increasing the L3T4 concentration to 1 µg/ml, increased the apoptotic cell death to approximately 70% and 40% respectively (FIG. 5). There was no obvious apoptosis observed in CD4/fas786A-23 cells treated similarly (FIGS. 4 and 5). Apoptosis induced through Fas was thus increased from 30%–40% in the controls to 60%–70% when FAF1 was expressed. Similar results were obtained in a human T cell leukemia line, Jurkat, where transient expression of FAF1 potentiated apoptosis induced by anti-human Fas antibody. These data indicate that FAF1 can potentiate apoptosis mediated by Fas and acts downstream of Fas.

The results indicate that FAF1 is a molecule which acts downstream in the Fas signal transduction pathway. FAF1 can interact selectively with the wild type cytoplasmic domain of Fas. This specific interaction occurred not only in yeast cells but also in mammalian cells. The binding is not the result of overexpression of FAF1 in Cos cells because the level of FAF1 expression was relatively low (approximately one tenth) compared to other proteins that were expressed with the same antibody tag. When expressed transiently in L cells, FAF1 was able to potentiate apoptosis induced by Fas.

All publications and patent documents cited herein are hereby incorporated by reference.

What is claimed is:

1. An isolated polypeptide comprising a domain of a Fas-associated factor 1 (FAF1) polypeptide, said polypeptide capable of associating with a cytoplasmic domain of Fas, wherein said FAF1 domain is encoded by a nucleic acid sequence that comprises at least 18 nucleotides and hybridizes under stringent conditions to the complementary nucleic acid sequence shown in SEQ ID NO: 1 or to a degenerate form thereof.

2. The polypeptide of claim 1, consisting of the amino acid sequence of SEQ ID NO:2.

3. The polypeptide of claim 1, further comprising an influenza virus HA epitope tag.

4. A kit useful for the prophylactic or therapeutic treatment of a disease resulting from dysregulated Fas-associated factor 1 (FAF1) polypeptide-potentiated apoptosis comprising a polypeptide of claim 1.

5. A pharmaceutical composition useful in the treatment of a disease resulting from dysregulated Fas-associated factor 1 (FAF1) polypeptide-potentiated apoptosis, comprising an isolated polypeptide comprising a domain of an FAF1 polypeptide, said polypeptide capable of associating with a cytoplasmic domain of Fas, wherein said FAF1 domain is encoded by a nucleic acid sequence that comprises at least 18 nucleotides and hybridizes under stringent conditions to the complementary nucleic acid sequence shown in SEQ ID NO:1 or to a degenerate form thereof, and a pharmaceutically acceptable carrier.

6. A fusion protein having at least two components, wherein a first component of the fusion protein comprises the polypeptide of claim 1.

7. The fusion protein of claim 6, wherein the fusion protein is FAF1-GAL4 activation domain.

8. The fusion protein of claim 6, wherein a second component of the fusion protein comprises a tag, a product of a second gene, or a product of a fragment of said second gene.

9. The fusion protein of claim 8, wherein the tag is GST, an epitope tag or an enzyme.

10. The fusion protein of claim 8, wherein the second gene is lacZ.

11. The polypeptide of claim 1, wherein the domain is encoded by a by a nucleic acid sequence that hybridizes under stringent conditions to the complete nucleic acid sequence shown in SEQ ID NO:1 or to a degenerate form thereof.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2558 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 413..2359

( x i ) SEQUENCE DESCRIPTION: SEQ ID NO:1:

| | | | | | | | |
|---|---|---|---|---|---|---|---|
| TCGAGCTACG | TCAGGGCTGG | AGGGAGCCGG | GCGCGCGCTG | TTCGCAACCT | GTCCTCCTCC | | 60 |
| CAGGCGGCGA | CGGAAGGACC | GGCCCGGCAT | CGAGACCAGC | CTCCCTCGCA | ACCTGTCCTC | | 120 |
| CTCCCAGGCG | GCGACGGAAG | GACCGGCCCG | GCATCGAGAC | CAGCCTCCCC | GTCCCGGCAG | | 180 |
| CTGCGGCGAG | GGCTCCGCGG | GGCGCAGGCG | GGCTCAGGGC | GGCTGAAGGT | TACCGAGTGC | | 240 |
| ATGAGCACCT | AGTCTCCCGC | GCTGCCCCGC | CCGCCGGTCC | GCCGGCCCCT | CCCGCCGGCT | | 300 |
| CGCCCGCCAG | CCCTTCGCCA | CCCGGCGGCG | GCCGCAGCTT | CGGCCGCAGG | AGGCGCCGTC | | 360 |
| TCGCTCCCAG | GTGCGCGCTT | CGTTCCCGGA | GCCGCGGAGC | TCGGCGGCCG | CC ATG Met 1 | | 415 |

```
GCG TCC AAC ATG GAT TTA CCG ATG ATC CTT GCG GAT TTT CAG GCA TGT                463
Ala Ser Asn Met Asp Leu Pro Met Ile Leu Ala Asp Phe Gln Ala Cys
          5               10                  15

ACT GGT ATT GAA AAC ATC GAT GAA GCT ATA ACA CTG CTT GAG CAA AAT                511
Thr Gly Ile Glu Asn Ile Asp Glu Ala Ile Thr Leu Leu Glu Gln Asn
         20                  25                  30

AAC TGG GAC TTG GTG GCA GCT ATT AAT GGT GTA ATA CCA CAG GAA AAT                559
Asn Trp Asp Leu Val Ala Ala Ile Asn Gly Val Ile Pro Gln Glu Asn
     35                  40                  45

GGC ATT CTA CAA AGT GAC TTT GGA GGT GAG ACC ATG CCA GGA CCC ACA                607
Gly Ile Leu Gln Ser Asp Phe Gly Gly Glu Thr Met Pro Gly Pro Thr
 50                  55                  60                  65

TTT GAT CCA GCA AGT CAC CCT GCT CCA GCT TCA ACT CCC TCT TCT TCA                655
Phe Asp Pro Ala Ser His Pro Ala Pro Ala Ser Thr Pro Ser Ser Ser
                 70                  75                  80

GCG TTT CGA CCT GTA ATG CCA TCC AGG CAG ATT GTA GAA AGG CAG CCT                703
Ala Phe Arg Pro Val Met Pro Ser Arg Gln Ile Val Glu Arg Gln Pro
             85                  90                  95

CGA ATG CTA GAC TTC AGA GTT GAA TAC AGA GAC AGA AAT GTT GAT GTG                751
Arg Met Leu Asp Phe Arg Val Glu Tyr Arg Asp Arg Asn Val Asp Val
        100                 105                 110

GTA CTT GAA GAC AGC TGT ACT GTT GGA GAG ATC AAA CAG ATT CTA GAA                799
Val Leu Glu Asp Ser Cys Thr Val Gly Glu Ile Lys Gln Ile Leu Glu
    115                 120                 125

AAT GAG CTT CAG ATA CCT GTG CCT AAA ATG CTG TTA AAA GGC TGG AAG                847
Asn Glu Leu Gln Ile Pro Val Pro Lys Met Leu Leu Lys Gly Trp Lys
130                 135                 140                 145

ACT GGA GAC GTG GAA GAC AGT ACG GTC TTA AAA TCA CTA CAC TTG CCA                895
Thr Gly Asp Val Glu Asp Ser Thr Val Leu Lys Ser Leu His Leu Pro
                150                 155                 160

AAA AAC AAC AGT CTT TAT GTC CTT ACA CCA GAC TTG CCA CCG CCT TCA                943
Lys Asn Asn Ser Leu Tyr Val Leu Thr Pro Asp Leu Pro Pro Pro Ser
            165                 170                 175

TCA TCC AGC CAT GCT GGT GCC CTG CAG GAA TCA TTA AAT CAA AAC TTC                991
Ser Ser Ser His Ala Gly Ala Leu Gln Glu Ser Leu Asn Gln Asn Phe
        180                 185                 190

ATG CTG ATC ATC ACC CAC CGA GAG GTC CAG CGG GAG TAC AAC CTG AAC                1039
Met Leu Ile Ile Thr His Arg Glu Val Gln Arg Glu Tyr Asn Leu Asn
    195                 200                 205

TTC TCA GGA AGC AGT ACC GTT CAA GAG GTA AAG AGA AAT GTG TAT GAC                1087
Phe Ser Gly Ser Ser Thr Val Gln Glu Val Lys Arg Asn Val Tyr Asp
210                 215                 220                 225

CTT ACA AGC ATA CCT GTT CGA CAT CAG TTA TGG GAG GGC TGG CCA GCT                1135
Leu Thr Ser Ile Pro Val Arg His Gln Leu Trp Glu Gly Trp Pro Ala
                230                 235                 240

TCT GCC ACC GAT GAC TCA ATG TGT CTT GCT GAA TCA GGC CTC TCT TAT                1183
Ser Ala Thr Asp Asp Ser Met Cys Leu Ala Glu Ser Gly Leu Ser Tyr
            245                 250                 255
```

-continued

| | | | | | | | | | | | | | | | | |
|---|---|---|---|---|---|---|---|---|---|---|---|---|---|---|---|---|
| CCC | TGC | CAT | CGA | TTA | ACT | GTG | GGA | AGA | AGA | ACT | TCA | CCT | GTA | CAG | ACC | 1231 |
| Pro | Cys | His | Arg | Leu | Thr | Val | Gly | Arg | Arg | Thr | Ser | Pro | Val | Gln | Thr | |
| | 260 | | | | 265 | | | | | | 270 | | | | | |
| CGT | GAG | CAA | TCA | GAA | GAG | CAA | AGC | ACG | GAT | GTT | CAT | ATG | GTT | AGT | GAT | 1279 |
| Arg | Glu | Gln | Ser | Glu | Glu | Gln | Ser | Thr | Asp | Val | His | Met | Val | Ser | Asp | |
| | 275 | | | | | 280 | | | | | 285 | | | | | |
| AGT | GAT | GGC | GAT | GAC | TTT | GAA | GAT | GCT | TCA | GAA | TTT | GGA | GTG | GAT | GAC | 1327 |
| Ser | Asp | Gly | Asp | Asp | Phe | Glu | Asp | Ala | Ser | Glu | Phe | Gly | Val | Asp | Asp | |
| 290 | | | | | 295 | | | | | 300 | | | | | 305 | |
| GGA | GAA | GTA | TTT | GGC | ATG | GCA | TCA | TCT | ACC | CTG | AGA | AAA | TCT | CCA | ATG | 1375 |
| Gly | Glu | Val | Phe | Gly | Met | Ala | Ser | Ser | Thr | Leu | Arg | Lys | Ser | Pro | Met | |
| | | | | 310 | | | | | 315 | | | | | 320 | | |
| ATG | CCA | GAA | AAC | GCA | GAA | AAT | GAA | GGA | GAT | GCC | TTA | TTA | CAA | TTT | ACA | 1423 |
| Met | Pro | Glu | Asn | Ala | Glu | Asn | Glu | Gly | Asp | Ala | Leu | Leu | Gln | Phe | Thr | |
| | | | 325 | | | | | 330 | | | | | 335 | | | |
| GCA | GAG | TTT | TCT | TCA | AGA | TAT | AGT | GAC | TGC | CAT | CCT | GTA | TTT | TAT | ATT | 1471 |
| Ala | Glu | Phe | Ser | Ser | Arg | Tyr | Ser | Asp | Cys | His | Pro | Val | Phe | Tyr | Ile | |
| | | 340 | | | | | 345 | | | | | 350 | | | | |
| GGC | TCA | TTA | GAA | GCT | GCT | TTC | CAA | GAG | GCC | TTC | TAT | GTG | AAA | GCC | CGA | 1519 |
| Gly | Ser | Leu | Glu | Ala | Ala | Phe | Gln | Glu | Ala | Phe | Tyr | Val | Lys | Ala | Arg | |
| | 355 | | | | | 360 | | | | | 365 | | | | | |
| GAC | AGA | AAA | CTT | CTT | GCT | ATC | TAC | CTC | CAC | CAT | GAT | GAA | AGT | GTA | CTA | 1567 |
| Asp | Arg | Lys | Leu | Leu | Ala | Ile | Tyr | Leu | His | His | Asp | Glu | Ser | Val | Leu | |
| 370 | | | | | 375 | | | | | 380 | | | | | 385 | |
| ACC | AAC | GTG | TTC | TGC | TCA | CAA | ATG | CTT | TGT | GCT | GAA | TCC | ATT | GTT | TCC | 1615 |
| Thr | Asn | Val | Phe | Cys | Ser | Gln | Met | Leu | Cys | Ala | Glu | Ser | Ile | Val | Ser | |
| | | | | 390 | | | | | 395 | | | | | 400 | | |
| TAT | CTG | AGT | CAA | AAT | TTT | ATA | ACC | TGG | GCT | TGG | GAT | CTG | ACA | AAG | GAC | 1663 |
| Tyr | Leu | Ser | Gln | Asn | Phe | Ile | Thr | Trp | Ala | Trp | Asp | Leu | Thr | Lys | Asp | |
| | | | 405 | | | | | 410 | | | | | 415 | | | |
| ACC | AAC | AGA | GCA | AGA | TTT | CTG | ACA | ATG | TGC | AAT | AGA | CAC | TTT | GGC | AGC | 1711 |
| Thr | Asn | Arg | Ala | Arg | Phe | Leu | Thr | Met | Cys | Asn | Arg | His | Phe | Gly | Ser | |
| | | 420 | | | | | 425 | | | | | 430 | | | | |
| GTT | ATT | GCA | CAA | ACT | ATT | CGG | ACT | CAA | AAG | ACA | GAT | CAG | TTT | CCA | CTT | 1759 |
| Val | Ile | Ala | Gln | Thr | Ile | Arg | Thr | Gln | Lys | Thr | Asp | Gln | Phe | Pro | Leu | |
| | 435 | | | | | 440 | | | | | 445 | | | | | |
| TTC | CTG | ATT | ATC | ATG | GGA | AAG | CGA | TCA | TCT | AAT | GAA | GTG | TTA | AAT | GTG | 1807 |
| Phe | Leu | Ile | Ile | Met | Gly | Lys | Arg | Ser | Ser | Asn | Glu | Val | Leu | Asn | Val | |
| 450 | | | | | 455 | | | | | 460 | | | | | 465 | |
| ATA | CAA | GGT | AAT | ACA | ACA | GTG | GAT | GAG | TTA | ATG | ATG | AGA | CTC | ATG | GCT | 1855 |
| Ile | Gln | Gly | Asn | Thr | Thr | Val | Asp | Glu | Leu | Met | Met | Arg | Leu | Met | Ala | |
| | | | | 470 | | | | | 475 | | | | | 480 | | |
| GCA | ATG | GAG | ATT | TTC | TCA | GCT | CAA | CAA | CAG | GAA | GAC | ATT | AAG | GAT | GAG | 1903 |
| Ala | Met | Glu | Ile | Phe | Ser | Ala | Gln | Gln | Gln | Glu | Asp | Ile | Lys | Asp | Glu | |
| | | | 485 | | | | | 490 | | | | | 495 | | | |
| GAT | GAA | CGT | GAA | GCC | AGA | GAA | AAT | GTG | AAG | AGA | GAG | CAA | GAT | GAG | GCC | 1951 |
| Asp | Glu | Arg | Glu | Ala | Arg | Glu | Asn | Val | Lys | Arg | Glu | Gln | Asp | Glu | Ala | |
| | | 500 | | | | | 505 | | | | | 510 | | | | |
| TAT | CGC | CTT | TCC | CTC | GAA | GCC | GAC | AGG | GCA | AAG | AGA | GAA | GCT | CAT | GAG | 1999 |
| Tyr | Arg | Leu | Ser | Leu | Glu | Ala | Asp | Arg | Ala | Lys | Arg | Glu | Ala | His | Glu | |
| | 515 | | | | | 520 | | | | | 525 | | | | | |
| AGA | GAG | ATG | GCA | GAA | CAG | TTT | CGT | TTG | GAG | CAG | ATT | CGC | AAA | GAA | CAA | 2047 |
| Arg | Glu | Met | Ala | Glu | Gln | Phe | Arg | Leu | Glu | Gln | Ile | Arg | Lys | Glu | Gln | |
| 530 | | | | | 535 | | | | | 540 | | | | | 545 | |
| GAA | GAA | GAA | CGT | GAG | GCC | ATC | AGA | CTC | TCC | TTA | GAA | CAA | GCC | CTT | CCT | 2095 |
| Glu | Glu | Glu | Arg | Glu | Ala | Ile | Arg | Leu | Ser | Leu | Glu | Gln | Ala | Leu | Pro | |
| | | | | 550 | | | | | 555 | | | | | 560 | | |
| CCA | GAG | CCG | AAG | GAA | GAA | AAT | GCT | GAG | CCT | GTT | AGC | AAG | CTT | CGG | ATT | 2143 |
| Pro | Glu | Pro | Lys | Glu | Glu | Asn | Ala | Glu | Pro | Val | Ser | Lys | Leu | Arg | Ile | |
| | | | 565 | | | | | 570 | | | | | 575 | | | |

-continued

```
CGA ACC CCC AGT GGC GAG TTC CTG GAA CGG CGT TTC CTG GCC AGC AAT    2191
Arg Thr Pro Ser Gly Glu Phe Leu Glu Arg Arg Phe Leu Ala Ser Asn
        580             585             590

AAG CTC CAG ATT GTC TTT GAT TTC GTG GCT TCC AAG GGA TTT CCA TGG    2239
Lys Leu Gln Ile Val Phe Asp Phe Val Ala Ser Lys Gly Phe Pro Trp
    595             600             605

GAT GAA TTC AAG TTA CTG AGC ACC TTT CCT AGG AGA GAT GTA ACT CAG    2287
Asp Glu Phe Lys Leu Leu Ser Thr Phe Pro Arg Arg Asp Val Thr Gln
610             615             620             625

CTA GAC CCC AAT AAG TCA TTA TTG GAG GTA AAC TTG TTC CCT CAA GAA    2335
Leu Asp Pro Asn Lys Ser Leu Leu Glu Val Asn Leu Phe Pro Gln Glu
                630             635             640

ACC CTT TTC CTT CAA GCA AAA GAG TAAACATGAC TGAGAGGTGG AAGCAGCCAC    2389
Thr Leu Phe Leu Gln Ala Lys Glu
                645

TCCTGACGAG CCAGCGGCAC GTGTCAAGAG ATGGGCTCCT CACCAACCCA CCTACCTGCT    2449

CGTGTCACTC AGTTCAATGT CACACTTCTG CCTCTTGCAA GATTGCTGGA AAAAAGTAAT    2509

AAACATAGCT ACTTAAAAAA AAAAAAAAAA AAACCCTGAC GTAGCTCGA               2558
```

( 2 ) INFORMATION FOR SEQ ID NO:2:

( i ) SEQUENCE CHARACTERISTICS:
        ( A ) LENGTH: 649 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ser Asn Met Asp Leu Pro Met Ile Leu Ala Asp Phe Gln Ala
 1               5                  10                  15

Cys Thr Gly Ile Glu Asn Ile Asp Glu Ala Ile Thr Leu Leu Glu Gln
            20                  25                  30

Asn Asn Trp Asp Leu Val Ala Ala Ile Asn Gly Val Ile Pro Gln Glu
        35                  40                  45

Asn Gly Ile Leu Gln Ser Asp Phe Gly Gly Glu Thr Met Pro Gly Pro
    50                  55                  60

Thr Phe Asp Pro Ala Ser His Pro Ala Pro Ala Ser Thr Pro Ser Ser
65                  70                  75                  80

Ser Ala Phe Arg Pro Val Met Pro Ser Arg Gln Ile Val Glu Arg Gln
                85                  90                  95

Pro Arg Met Leu Asp Phe Arg Val Glu Tyr Arg Asp Arg Asn Val Asp
            100                 105                 110

Val Val Leu Glu Asp Ser Cys Thr Val Gly Glu Ile Lys Gln Ile Leu
        115                 120                 125

Glu Asn Glu Leu Gln Ile Pro Val Pro Lys Met Leu Leu Lys Gly Trp
    130                 135                 140

Lys Thr Gly Asp Val Glu Asp Ser Thr Val Leu Lys Ser Leu His Leu
145                 150                 155                 160

Pro Lys Asn Asn Ser Leu Tyr Val Leu Thr Pro Asp Leu Pro Pro Pro
                165                 170                 175

Ser Ser Ser Ser His Ala Gly Ala Leu Gln Glu Ser Leu Asn Gln Asn
            180                 185                 190

Phe Met Leu Ile Ile Thr His Arg Glu Val Gln Arg Glu Tyr Asn Leu
        195                 200                 205

Asn Phe Ser Gly Ser Ser Thr Val Gln Glu Val Lys Arg Asn Val Tyr
    210                 215                 220
```

-continued

| | | | | | | | | | | | | | | | |
|---|---|---|---|---|---|---|---|---|---|---|---|---|---|---|---|
| Asp | Leu | Thr | Ser | Ile | Pro | Val | Arg | His | Gln | Leu | Trp | Glu | Gly | Trp | Pro |
| 225 | | | | | 230 | | | | | 235 | | | | | 240 |
| Ala | Ser | Ala | Thr | Asp | Asp | Ser | Met | Cys | Leu | Ala | Glu | Ser | Gly | Leu | Ser |
| | | | | 245 | | | | | 250 | | | | | 255 | |
| Tyr | Pro | Cys | His | Arg | Leu | Thr | Val | Gly | Arg | Arg | Thr | Ser | Pro | Val | Gln |
| | | | | 260 | | | | | 265 | | | | | 270 | |
| Thr | Arg | Glu | Gln | Ser | Glu | Glu | Gln | Ser | Thr | Asp | Val | His | Met | Val | Ser |
| | | 275 | | | | | 280 | | | | | 285 | | | |
| Asp | Ser | Asp | Gly | Asp | Asp | Phe | Glu | Asp | Ala | Ser | Glu | Phe | Gly | Val | Asp |
| | | 290 | | | | 295 | | | | | 300 | | | | |
| Asp | Gly | Glu | Val | Phe | Gly | Met | Ala | Ser | Ser | Thr | Leu | Arg | Lys | Ser | Pro |
| 305 | | | | | 310 | | | | | 315 | | | | | 320 |
| Met | Met | Pro | Glu | Asn | Ala | Glu | Asn | Glu | Gly | Asp | Ala | Leu | Leu | Gln | Phe |
| | | | | 325 | | | | | 330 | | | | | 335 | |
| Thr | Ala | Glu | Phe | Ser | Ser | Arg | Tyr | Ser | Asp | Cys | His | Pro | Val | Phe | Tyr |
| | | | 340 | | | | | 345 | | | | | 350 | | |
| Ile | Gly | Ser | Leu | Glu | Ala | Ala | Phe | Gln | Glu | Ala | Phe | Tyr | Val | Lys | Ala |
| | | | 355 | | | | | 360 | | | | | 365 | | |
| Arg | Asp | Arg | Lys | Leu | Leu | Ala | Ile | Tyr | Leu | His | His | Asp | Glu | Ser | Val |
| | | 370 | | | | | 375 | | | | | 380 | | | |
| Leu | Thr | Asn | Val | Phe | Cys | Ser | Gln | Met | Leu | Cys | Ala | Glu | Ser | Ile | Val |
| 385 | | | | | 390 | | | | | 395 | | | | | 400 |
| Ser | Tyr | Leu | Ser | Gln | Asn | Phe | Ile | Thr | Trp | Ala | Trp | Asp | Leu | Thr | Lys |
| | | | | 405 | | | | | 410 | | | | | 415 | |
| Asp | Thr | Asn | Arg | Ala | Arg | Phe | Leu | Thr | Met | Cys | Asn | Arg | His | Phe | Gly |
| | | | 420 | | | | | 425 | | | | | 430 | | |
| Ser | Val | Ile | Ala | Gln | Thr | Ile | Arg | Thr | Gln | Lys | Thr | Asp | Gln | Phe | Pro |
| | | | 435 | | | | | 440 | | | | | 445 | | |
| Leu | Phe | Leu | Ile | Ile | Met | Gly | Lys | Arg | Ser | Ser | Asn | Glu | Val | Leu | Asn |
| | 450 | | | | | 455 | | | | | 460 | | | | |
| Val | Ile | Gln | Gly | Asn | Thr | Thr | Val | Asp | Glu | Leu | Met | Met | Arg | Leu | Met |
| 465 | | | | | 470 | | | | | 475 | | | | | 480 |
| Ala | Ala | Met | Glu | Ile | Phe | Ser | Ala | Gln | Gln | Gln | Glu | Asp | Ile | Lys | Asp |
| | | | | 485 | | | | | 490 | | | | | 495 | |
| Glu | Asp | Glu | Arg | Glu | Ala | Arg | Glu | Asn | Val | Lys | Arg | Glu | Gln | Asp | Glu |
| | | | 500 | | | | | 505 | | | | | 510 | | |
| Ala | Tyr | Arg | Leu | Ser | Leu | Glu | Ala | Asp | Arg | Ala | Lys | Arg | Glu | Ala | His |
| | | 515 | | | | | 520 | | | | | 525 | | | |
| Glu | Arg | Glu | Met | Ala | Glu | Gln | Phe | Arg | Leu | Glu | Gln | Ile | Arg | Lys | Glu |
| | | 530 | | | | | 535 | | | | | 540 | | | |
| Gln | Glu | Glu | Glu | Arg | Glu | Ala | Ile | Arg | Leu | Ser | Leu | Glu | Gln | Ala | Leu |
| 545 | | | | | 550 | | | | | 555 | | | | | 560 |
| Pro | Pro | Glu | Pro | Lys | Glu | Glu | Asn | Ala | Glu | Pro | Val | Ser | Lys | Leu | Arg |
| | | | | 565 | | | | | 570 | | | | | 575 | |
| Ile | Arg | Thr | Pro | Ser | Gly | Glu | Phe | Leu | Glu | Arg | Arg | Phe | Leu | Ala | Ser |
| | | | 580 | | | | | 585 | | | | | 590 | | |
| Asn | Lys | Leu | Gln | Ile | Val | Phe | Asp | Phe | Val | Ala | Ser | Lys | Gly | Phe | Pro |
| | | 595 | | | | | 600 | | | | | 605 | | | |
| Trp | Asp | Glu | Phe | Lys | Leu | Leu | Ser | Thr | Phe | Pro | Arg | Arg | Asp | Val | Thr |
| | 610 | | | | | 615 | | | | | 620 | | | | |
| Gln | Leu | Asp | Pro | Asn | Lys | Ser | Leu | Leu | Glu | Val | Asn | Leu | Phe | Pro | Gln |
| 625 | | | | | 630 | | | | | 635 | | | | | 640 |
| Glu | Thr | Leu | Phe | Leu | Gln | Ala | Lys | Glu | | | | | | | |
| | | | | 645 | | | | | | | | | | | |

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Arg  Ser  Pro  Leu
    1

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly  Cys  Arg  Asn  Ser  Ile
    1                      5